US006838256B2

(12) United States Patent
Murphy et al.

(10) Patent No.: US 6,838,256 B2
(45) Date of Patent: Jan. 4, 2005

(54) CODING SEQUENCES OF THE HUMAN BRCA1 GENE

(75) Inventors: Patricia D. Murphy, Slingerland, NY (US); Antonette C. Allen, Severn, MD (US); Christopher P. Alvares, Potomac, MD (US); Brenda S. Critz, Frederick, MD (US); Sheri J. Olson, Arlington, VA (US); Denise B. Schelter, Silver Spring, MD (US); Bin Zeng, Rockville, MD (US)

(73) Assignee: Gene Logic Inc., Gaithersburg, MD (US)

( * ) Notice: Subject to any disclaimer, the term of this patent is extended or adjusted under 35 U.S.C. 154(b) by 182 days.

(21) Appl. No.: 09/734,672

(22) Filed: Dec. 13, 2000

(65) Prior Publication Data

US 2002/0183268 A1 Dec. 5, 2002

Related U.S. Application Data

(63) Continuation of application No. 08/966,436, filed on Nov. 7, 1997, now abandoned, which is a continuation-in-part of application No. 08/598,591, filed on Feb. 12, 1996, now Pat. No. 5,654,155.

(51) Int. Cl.[7] .......................... C12P 21/06; C12N 5/00; C12N 15/00; C12N 15/63; C07H 21/02
(52) U.S. Cl. .................. 435/69.1; 425/320.1; 425/325; 425/455; 425/252.1; 425/471; 536/23.1; 536/23.5
(58) Field of Search ............................. 435/69.1, 320.1, 435/325, 455, 252.1, 471; 536/23.1, 23.5

(56) References Cited

U.S. PATENT DOCUMENTS

| 4,683,202 A | 7/1987 | Mullis .......................... 435/91 |
| 5,455,934 A | 10/1995 | Holland et al. ............. 395/404 |
| 5,510,270 A | 4/1996 | Fodor et al. ................ 436/518 |
| 5,545,531 A | 8/1996 | Rava et al. ..................... 435/6 |
| 5,547,839 A | 8/1996 | Dower et al. .................. 435/6 |
| 5,561,058 A | 10/1996 | Gelfand et al. ............ 435/912 |
| 5,582,989 A | 12/1996 | Caskey et al. ................. 435/6 |
| 5,589,330 A | 12/1996 | Shuber .......................... 435/5 |
| 5,624,803 A | 4/1997 | Noonberg et al. ............. 435/6 |
| 5,633,134 A | 5/1997 | Shuber .......................... 435/6 |
| 5,650,316 A | 7/1997 | Aggarwal et al. .......... 435/375 |
| 5,693,473 A | * 12/1997 | Shattuck-Eidens et al. ..... 435/6 |
| 5,710,001 A | 1/1998 | Skolnick ........................ 435/6 |
| 5,726,019 A | 3/1998 | Sidranshy ...................... 435/6 |
| 5,747,282 A | 5/1998 | Skolnick .................... 435/69.1 |
| 5,750,400 A | 5/1998 | Murphy et al. ................ 435/6 |
| 5,753,441 A | 5/1998 | Skolnick ........................ 435/6 |
| 5,756,294 A | 5/1998 | White et al. ................... 435/6 |
| 5,858,669 A | 1/1999 | Levine ........................... 435/6 |
| 5,891,857 A | 4/1999 | Holt et al. .................... 514/44 |
| 5,912,127 A | 6/1999 | Narod et al. ................... 435/6 |
| 5,948,643 A | 9/1999 | Rubinfeld et al. ......... 435/69.1 |
| 5,965,377 A | 10/1999 | Adams et al. ............. 435/7.23 |
| 6,033,857 A | 3/2000 | Tavtigian et al. ............... 435/6 |
| 6,045,997 A | 4/2000 | Futreal et al. .................. 435/6 |
| 6,051,379 A | 4/2000 | Lescallett et al. .............. 435/6 |
| 6,083,698 A | 7/2000 | Olson et al. ................... 435/6 |
| 6,124,104 A | 9/2000 | Tavtigian et al. ............ 435/7.2 |
| 6,130,322 A | 10/2000 | Murphy et al. ............ 536/23.1 |

FOREIGN PATENT DOCUMENTS

| EP | 0705902 A1 | 10/1996 |
| GB | 2307477 A | 5/1997 |
| WO | WO9304200 | 3/1993 |
| WO | WO 96/05306 | * 2/1996 |
| WO | WO9722689 | 6/1997 |
| WO | WO9730108 | 8/1997 |
| WO | WO9815654 | 4/1998 |

OTHER PUBLICATIONS

PTO sequence search report, Mar. 2004.*
Verma et al, Gene Therapy–promises, problems and prospects. NATURE 389:239–242, 1997.*
Wood. Phenotype Assesment: Are you missing something? COMP. MED. 50(1): 12–15, 2000.*
Wall RJ. Transgenic livestock: Progress and prospects for the future. THERIOGENOLOGY 45:57–68, 1996.*
Kappel et al. Regulating gene expression in transgenic animals. Current Opinion in Biotechnology 3:558–553 1992.*
Ngo, Computational complexity Protein structure prediction and the Levinthal paradox in The Protein Folding Problem and Tertiary Structure Prediction, Merz et al. (eds), Birkhauser Boston: Boston, MA, pp. 443 and 492–495, 1994).
Rudinger Characteristics of amino acids as components of a peptide hormone sequence (in Peptide Hormones, Parsons (ed.), University Park Press: Baltimore, MD, pp. 1–7, 1976).
Yassaee et al Novel mutations in the BRCA1 and BRCA2 genes in Iranian women with early–onset breast cancer. Breast Cancer Res. 2002;4(4):R6. Epub 2002 Apr. 16.*

(List continued on next page.)

*Primary Examiner*—Jeffrey Fredman
*Assistant Examiner*—Sumesh Kaushal
(74) *Attorney, Agent, or Firm*—Morgan Lewis & Bockius LLP

(57) ABSTRACT isolated coding sequences and to the protein sequences they code for. This invention is directed to three coding sequence of the BRCA1 gene. The three coding sequences, BRCA1[(omi1)], BRCA1[(omi2)], and BRCA1[(omi3)] and their frequencies of occurrence are provided together with the protein sequences they code for. Another aspect of this invention is a method of determining the consensus sequence for any gene. Another aspect of the invention is a method of identifying an individual having an increased genetic susceptibility to breast or ovarian cancer because they have inherited a causative mutation in their BRCA1 gene. This invention is also related to a method of performing gene therapy with any of the isolated BRCA1 coding sequences.

16 Claims, 1 Drawing Sheet

OTHER PUBLICATIONS

Montagna et al Identification of BRCA1 and BRCA2 carriers by allele–specific gene expression (AGE) analysis Int J Cancer. Apr. 10, 2002;98(5):732–6.*

Rosenberg et al, Gene Therapist, Heal Thyself. SCIENCE 287:1751, 2000.*

Anderson WF, Human Gene Therapy. NATURE 392:25–30, 1998.*

Abeliovich et al. (1997) The Founder Mutations 185delAG and 5382insCin BRCA and 6174delT in BRCA2 Appear in 60% of Ovarian Cancer and 30% of Early–Onset Breast Cancer Patients among Ashkenazi Women. *Am. J. Hum. Genetics* 60(3): 505–514.

Bertwistle et al. (1998) Functions of the BRCA1 and BRCA2 genes. *Current Opinion Genet. Dev.* 8(1):14–20.

Friedman et al. (1994) Confirmation of BRCA1 by analysis of germline mutations linked to breast and ovarian cancer in ten families. *Nature Genetics* 8(4):399–404.

Funari et al. (1997) Growth suppression of glioma cells by PTEN requires functional phosphatase catalytic domain. *Proceedings of the National Academy of Sciences (USA)* 94(23): 12479–12484.

Hacia et al. (1996) Detection of heterozygous mutations in BRCA1 using high density oligonucleotide arrays and two–colour fluorescence analysis. *Nature Genetics* 14(4):441–447.

Hogervorst et al. (1995) Rapid detection of BRCA1 mutations by the protein truncation test. *Nature Genetics* 10(2): 208–212.

Husain et al. (1998) BRCA1 Up–Regulation Is Associated with Repair–mediated Resistance to cis–Diamminedichloroplatinum (II)[1] *Cancer Research* 58(6): 1120–1123.

Ruffner et al. (1997) BRCA1 is a Cell Cycle–Regulated Nuclear Phosphoprotein. *Proceedings of the National Academy of Sciences (USA)* 94(14): 7138–7143.

Shattuck–Eidens et al. (1995) A Collaborative Survey of 80 Mutations in the BRCA1 Breast and Ovarian Cancer Susceptibility Gene. *Journal of the American Medical Association* 273(7): 535–541.

Struewing et al. (1995) The Carrier Frequency of the BRCA1 185delAG Mutation is Approximately 1 Percent in Ashkenazi Jewish Individuals. *Nature Genetics* 11(2):198–200.

Tashiro et al. (1997) Mutations in PTEN Are Frequent in Endometrial Carcinoma But Rare in Other Common Gynecological Malignancies[1]. *Cancer Research* 57(18): 3935–3940.

Thompson et al. (1995) Decreased Expression of BRCA1 Accelerates Growth and is Often Present During Sporadic Breast Cancer Progression. *Nature Genetics* 9(4):444–450.

Zhang et al (1998) BRCA1, BRCA2, and DNA Damage Response: Collision or Collusion? *Cell* 92(4): 433–436.

* cited by examiner

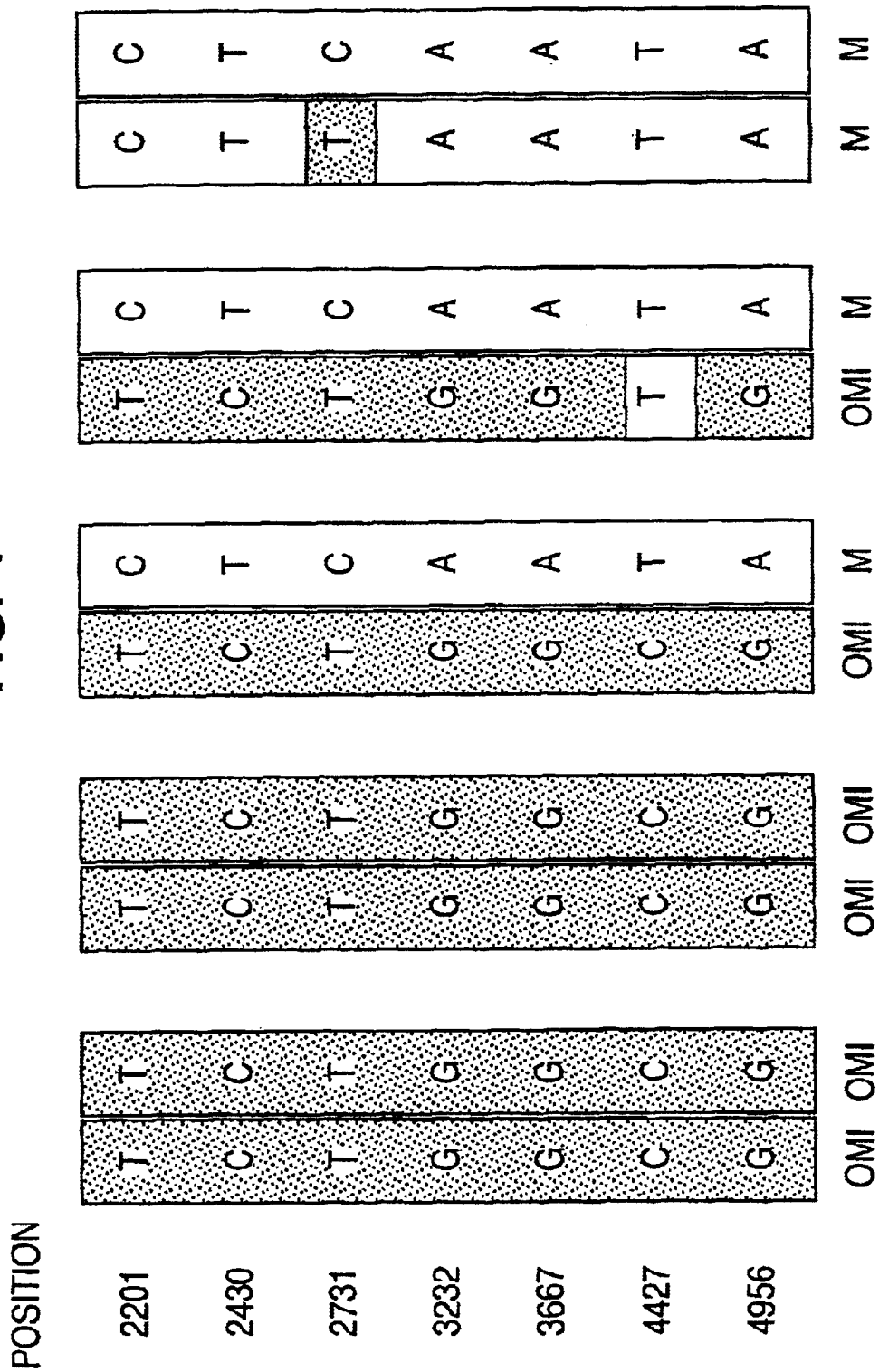

CODING SEQUENCES OF THE HUMAN BRCA1 GENE

CROSS REFERENCE TO RELATED APPLICATIONS

This application is a continuation patent application under 37 C.F.R. §1.53(b), of pending prior U.S. application Ser. No. 08/966,436, filed on Nov. 7, 1997 now abandoned, which is a continuation-in-part of U.S. application Ser. No. 08/598,591, filed on Feb. 12, 1996 now U.S. Pat. No. 5,654,155, both of which are herein incorporated by reference in their entirety.

FIELD OF THE INVENTION

This invention relates to a gene which has been associated with breast and ovarian cancer where the gene is found to be mutated. More specifically, this invention relates to the three coding sequences of the BRCA1 gene BRCA1$^{(omi1)}$, BRCA1$^{(omi2)}$, and BRCA1$^{(omi3)}$) isolated from human subjects.

BACKGROUND OF THE INVENTION

It has been estimated that about 5–10% of breast cancer is inherited Rowell, S., et al., *American Journal of Human Genetics* 55:861–865 (1994). Located on chromosome 17, BRCA1 is the first gene identified to be conferring increased risk for breast and ovarian cancer. Miki et al., *Science* 266:66–71 (1994). Mutations in this "tumor suppressor" gene are thought to account for roughly 45% of inherited breast cancer and 80–90% of families with increased risk of early onset breast and ovarian cancer. Easton et al., *American Journal of Human Genetics* 52:678–701 (1993).

Locating one or more mutations in the BRCA1 region of chromosome 17 provides a promising approach to reducing the high incidence and mortality associated with breast and ovarian cancer through the early detection of women at high risk. These women, once identified, can be targeted for more aggressive prevention programs. Screening is carried out by a variety of methods which include karyotyping, probe binding and DNA sequencing.

In DNA sequencing technology, genomic DNA is extracted from whole blood and the coding sequences of the BRCA1 gene are amplified. The coding sequences might be sequenced completely and the results are compared to the DNA sequence of the gene. Alternatively, the coding sequence of the sample gene may be compared to a panel of known mutations before completely sequencing the gene and comparing it to a normal sequence of the gene.

If a mutation in the BRCA1 coding sequence is found, it may be possible to provide the individual with increased expression of the gene through gene transfer therapy. It has been demonstrated that the gene transfer of the BRCA1 coding sequence into cancer cells inhibits their growth and reduces tumorigenesis of human cancer cells in nude mice. Jeffrey Holt and his colleagues conclude that the product of BRCA1 expression is a secreted tumor growth inhibitor, making BRCA1 an ideal gene for gene therapy studies. Transduction of only a moderate percentage of tumor cells apparently produces enough growth inhibitor to inhibit all tumor cells. Arteaga, C L, and J T Holt Cancer Research 56: 1098–1103 (1996), Holt, J T et al., Nature Genetics 12: 298–302 (1996).

The observation of Holt et al, that the BRCA1 growth inhibitor is a secreted protein leads to the possible use of injection of the growth inhibitor into the area of the tumor for tumor suppression.

The BRCA1 gene is divided into 24 separate exons. Exons 1 and 4 are noncoding, in that they are not part of the final functional BRCA1 protein product. The BRCA1 coding sequence spans roughly 5600 base pairs (bp). Each exon consists of 200–400 bp, except for exon 11 which contains about 3600 bp. To sequence the coding sequence of the BRCA1 gene, each exon is amplified separately and the resulting PCR products are sequenced in the forward and reverse directions. Because exon 11 is so large, we have divided it into twelve overlapping PCR fragments of roughly 350 bp each (segments "A" through "L" of BRCA1 exon 11).

Many mutations and polymorphisms have already been reported in the BRCA1 gene. A world wide web site has been built to facilitate the detection and characterization of alterations in breast cancer susceptibility genes. Such mutations in BRCA1 can be accessed through the Breast Cancer Information Core web site. This data site became publicly available on Nov. 1, 1995. Friend, S. et al. *Nature Genetics* 11:238, (1995).

The genetics of Breast/Ovarian Cancer Syndrome is autosomal dominant with reduced penetrance. In simple terms, this means that the syndrome runs through families such that both sexes can be carriers (only women get the disease but men can pass it on), all generations will likely have breast/ovarian or both diseases and sometimes in the same individual, occasionally women carriers either die young before they have the time to manifest disease (and yet offspring get it) or they never develop breast or ovarian cancer and die of old age (the latter people are said to have "reduced penetrance" because they never develop cancer). Pedigree analysis and genetic counseling is absolutely essential to the proper workup of a family prior to any lab work.

Until now, only a single coding sequence for the BRCA1 gene has been available for comparison to patient samples. That sequence is available as GenBank Accession Number U14680. There is a need in the art, therefore, to have available a coding sequence which is the BRCA1 coding sequence found in the majority of the population, a "consensus coding sequence", BRCA1$^{(omi1)}$ Seq. ID. NO. 1. A consensus coding sequence will make it possible for true mutations to be easily identified or differentiated from polymorphisms. Identification of mutations of the BRCA1 gene and protein would allow more widespread diagnostic screening for hereditary breast and ovarian cancer than is currently possible. Two additional coding sequences have been isolated and characterize. The BRCA1$^{(omi2)}$ SEQ. ID. NO.: 3, and BRCA1$^{(omi3)}$ SEQ. ID. NO.:5 coding sequences also have utility in diagnosis, gene therapy and in making therapeutic BRCA1 protein.

A coding sequence of the BRCA1 gene which occurs most commonly in the human gene pool is provided. The most commonly occurring coding sequence more accurately reflects the most likely sequence to be found in a subject. Use of the coding sequence BRCA1$^{(omi1)}$ SEQ. ID. NO.: 1, rather than the previously published BRCA1 sequence, will reduce the likelihood of misinterpreting a. "sequence variation" found in the population (i.e. polymorphism) with a pathologic "mutation" (i.e. causes disease in the individual or puts the individual at a high risk of developing the disease). With large interest in breast cancer predisposition testing, misinterpretation is particularly worrisome. People who already have breast cancer are asking the clinical question: "is my disease caused by a heritable genetic mutation?" The relatives of the those with breast cancer are asking the question: "Am I also a carrier of the mutation my relative has? Thus, is my risk increased, and should I undergo a more aggressive surveillance program."

SUMMARY OF THE INVENTION

The present invention is based on the isolation of three coding sequences of the BRCA1 gene found in human individuals.

It is an object of the invention to provide the most commonly occurring coding sequence of the BRCA1 gene.

It is another object of this invention to provide two other coding sequences of BRCA1 gene.

It is another object of the invention to provide three protein sequences coded for by three of the coding sequences of the BRCA1 gene.

It is another object of the invention to provide a list of the codon pairs which occur at each of seven polymorphic points on the BRCA1 gene.

It is another object of the invention to provide the rates of occurrence for the codons.

It is another object of the invention to provide a method wherein BRCA1, or parts thereof, is amplified with one or more oligonucleotide primers.

It is another object of this invention to provide a method of identifying individuals who carry no mutation(s) of the BRCA1 coding sequence and therefore have no increased genetic susceptibility to breast or ovarian cancer based on their BRCA1 genes.

It is another object of this invention to provide a method of identifying a mutation leading to an increased genetic susceptibility to breast or ovarian cancer.

There is a need in the art for a sequence of the BRCA1 gene and for the protein sequence of BRCA1 as well as for an accurate list of codons which occur at polymorphic points on a sequence.

A person skilled in the art of genetic susceptibility testing will find the present invention useful for:

a) identifying individuals having a BRCA1 gene with no coding mutations, who therefore cannot be said to have an increased genetic susceptibility to breast or ovarian cancer from their BRCA1 genes;

b) avoiding misinterpretation of polymorphisms found in the BRCA1 gene;

c) determining the presence of a previously unknown mutation in the BRCA1 gene.

d) identifying a mutation which increases the genetic susceptibility to breast or ovarian cancer.

e) probing a human sample of the BRCA1 gene.

f) performing gene therapy.

g) for making a functioning tumor growth inhibitor protein coded for by one of the BRCA1$^{omi}$ genes.

BRIEF DESCRIPTION OF THE FIGURE

As shown in FIG. 1, the alternative alleles at polymorphic (non-mutation causing variations) sites along a chromosome can be represented as a "haplotype" within a gene such as BRCA1. The BRCA1$^{(omi1)}$ haplotype is shown in FIG. 1 with dark shading (encompassing the alternative alleles found at nucleotide sites 2201, 2430, 2731, 3232, 3667, 4427, and 4956). For comparison, the haplotype that is in GenBank is shown with no shading. As can be seen from the figure, the common "consensus" haplotype is found intact in five separate chromosomes labeled with the OMI symbol (numbers 1–5 from left to right). Two additional haplotypes (BRCA1$^{(omi2)}$, and BRCA1$^{(omi3)}$ are represented with mixed dark and light shading (numbers 7 and 9 from left to right). In total, 7 of 10 haplotypes along the BRCA1 gene are unique.

DETAILED DESCRIPTION OF THE INVENTION

Definitions

The following definitions are provided for the purpose of understanding this invention.

"Breast and Ovarian cancer" is understood by those skilled in the art to include breast and ovarian cancer in women and also breast and prostate cancer in men. BRCA1 is associated genetic susceptibility to inherited breast and ovarian cancer in women and also breast and prostate cancer in men. Therefore, claims in this document which recite breast and/or ovarian cancer refer to breast, ovarian and prostate cancers in men and women.

"Coding sequence" or "DNA coding sequence" refers to those portions of a gene which, taken together, code for a peptide (protein), or which nucleic acid itself has function.

"Protein" or "peptide" refers to a sequence amino acids which has function.

"BRCA1$^{(omi)}$" refers collectively to the "BRCA1$^{(omi1)}$", "BRCA1$^{(omi2)}$" and "BRCA1$^{(omi3)}$" coding sequences.

"BRCA1$^{(omi1)}$" refers to SEQ. ID. NO.: 1, a coding sequence for the BRCA1 gene. The coding sequence was found by end to end sequencing of BRCA1 alleles from individuals randomly drawn from a Caucasian population found to have no family history of breast or ovarian cancer. The sequenced gene was found not to contain any mutations. BRCA1$^{(omi1)}$ was determined to be a consensus sequence by calculating the frequency with which the coding sequence occurred among the sample alleles sequenced.

"BRCA1$^{(omi2)}$" and "BRCA1$^{(omi3)}$" refer to SEQ. ID. NO.: 3, and SEQ. ID. NO.: 5 respectively. They are two additional coding sequences for the BRCA1 gene which were also isolated from individuals randomly drawn from a Caucasian population found to have no family history of breast or ovarian cancer. polymorphisms "Primer" as used herein refers to a sequence comprising about 20 or more nucleotides of the BRCA1 gene.

"Genetic susceptibility" refers to the susceptibility to breast or ovarian cancer due to the presence of a mutation in the BRCA1 gene.

A "target polynucleotide" refers to the nucleic acid sequence of interest e.g., the BRCA1 encoding polynucleotide. Other primers which can be used for primer hybridization will be known or readily ascertainable to those of skill in the art.

"Consensus" means the most commonly occurring in the population.

"Consensus genomic sequence" means the allele of the target gene which occurs with the greatest frequency in a population of individuals having no family history of disease associated with the target gene.

"Substantially complementary to" refers to a probe or primer sequences which hybridize to the sequences provided under stringent conditions and/or sequences having sufficient homology with BRCA1 sequences, such that the allele specific oligonucleotide probe or primers hybridize to the BRCA1 sequences to which they are complimentary.

"Haplotype" refers to a series of alleles within a gene on a chromosome.

"Isolated" as used herein refers to substantially free of other nucleic acids, proteins, lipids, carbohydrates or other materials with which they may be associated. Such association is typically either in cellular material or in a synthesis medium.

"Mutation" refers to a base change or a gain or loss of base pair(s) in a DNA sequence, which results in a DNA sequence which codes for a non-functioning protein or a protein with substantially reduced or altered function.

"Polymorphism" refers to a base change which is not associated with known pathology.

"Tumor growth inhibitor protein" refers to the protein coded for by the BRCA1 gene. The functional protein is thought to suppress breast and ovarian tumor growth.

The invention in several of its embodiments includes:

1. An isolated consensus DNA sequence of the BRCA1 coding sequence as set forth in SEQ. ID. NO.: 1.
2. A consensus protein sequence of the BRCA1 protein as set forth in SEQ. ID. NO.: 2.
3. An isolated coding sequence of the BRCA1 gene as set forth in SEQ. ID. NO.: 3.
4. A protein sequence of the BRCA1 protein as set forth in SEQ. ID. NO.: 4.
5. An isolated coding sequence of the BRCA1 gene as set forth in SEQ. ID. NO.: 5.
6. A protein sequence of the BRCA1 protein as set forth in SEQ. ID. NO.: 6.
7. A BRCA1 gene with a BRCA1 coding sequence not associated with breast or ovarian cancer which comprises an alternative pair of codons, AGC and AGT, which occur at position 2201 at frequencies of about 35–45%, and from about 55–65%, respectively.
8. A BRCA1 gene according to claim 7 wherein AGC occurs at a frequency of about 40%.
9. A set of at least two alternative codon pairs which occur at polymorphic positions in a BRCA1 gene with a BRCA1 coding sequence not associated with breast or ovarian cancer, wherein codon pairs are selected from the group consisting of:
   AGC and AGT at position 2201;
   TTG and CTG at position 2430;
   CCG and CTG at position 2731;
   GAA and GGA at position 3232;
   AAA and AGA at position 3667;
   TCT and TCC at position 4427; and
   AGT and GGT at position 4956.
10. A set of at least two alternative codon pairs according to claim 9, wherein the codon pairs occur in the following frequencies, respectively, in a population of individuals free of disease:
   at position 2201, AGC and AGT occur at frequencies from about 35–45%, and from about 55–65%, respectively;
   at position 2430, TTG and CTG occur at frequencies from about 35–45%, and from about 55–65%, respectively;
   at position 2731, CCG and CTG occur at frequencies from about 25–35%, and from about 65–75%, respectively;
   at position 3232, GAA and GGA occur at frequencies from about 35–45%, and from about 55–65%, respectively;
   at position 3667, AAA and AGA occur at frequencies from about 35–45%, and from about 55–65%, respectively;
   at position 4427, TCT and TCC occur at frequencies from about 45–55%, and from about 45–55%, respectively; and
   at position 4956, AGT and GGT occur at frequencies from about 35–45%, and from about 55–65%, respectively.
11. A set according to claim 10 which is at least three codon pairs.
12. A set according to claim 10 which is at least four codon pairs.
13. A set according to claim 10 which is at least five codon pairs.
14. A set according to claim 10 which is at least six codon pairs.
15. A set according to claim 10 which is at least seven codon pairs.
16. A method of identifying individuals having a BRCA1 gene with a BRCA1 coding sequence not associated with disease, comprising:
   (a) amplifying a DNA fragment of an individual's BRCA1 coding sequence using an oligonucleotide primer which specifically hybridizes to sequences within the gene;
   (b) sequencing said amplified DNA fragment by dideoxy sequencing;
   (c) repeating steps (a) and (b) until said individual's BRCA1 coding sequence is completely sequenced;
   (d) comparing the sequence of said amplified DNA fragment to a BRCA1$^{(omi)}$ DNA sequence, SEQ. ID. NO1, SEQ. ID. NO3, or SEQ. ID. NO5;
   (e) determining the presence or absence of each of the following polymorphic variation in said individual's BRCA1 coding sequence:
   AGC and AGT at position 2201,
   TTG and CTG at position 2430,
   CCG and CTG at position 2731,
   GAA and GGA at position 3232,
   AAA and AGA at position 3667,
   TCT and TCC at position 4427, and
   AGT and GGT at position 4956;
   (f) determining any sequence differences between said individual's BRCA1 coding sequences and SEQ. ID. NO1, SEQ. ID. NO3, or SEQ. ID. NO5 wherein the presence of said polymorphic variations and the absence of a variation outside of positions 2201, 2430, 2731, 3232, 3667, 4427, and 4956, is correlated with an absence of increased genetic susceptibility to breast or ovarian cancer resulting from a BRCA1 mutation in the BRCA1 coding sequence.
17. A method of claim 16 wherein, codon variations occur at the following frequencies, respectively, in a population of individuals free of disease:
   at position 2201, AGC and AGT occur at frequencies from about 35–45%, and from about 55–65%, respectively;
   at position 2430, TTG and CTG occur at frequencies from about 35–45%, and from about 55–65%, respectively;
   at position 2731, CCG and CTG occur at frequencies from about 25–35%, and from about 65–75%, respectively;
   at position 3232, GAA and GGA occur at frequencies from about 35–45%, and from about 55–65%, respectively;
   at position 3667, AAA and AGA occur at frequencies from about 35–45%, and from about 55–65%, respectively;
   at position 4427, TCT and TCC occur at frequencies from about 45–55%, and from about 45–55%, respectively; and
   at position 4956, AGT and GGT occur at frequencies from about 35–45%, and from about 55–65%, respectively.

18. A method according to claim 16 wherein said oligonucleotide primer is labeled with a radiolabel, a fluorescent label a bioluminescent label, a chemiluminescent label, or an enzyme label.

19. A method of detecting a increased genetic susceptibility to breast and ovarian cancer in an individual resulting from the presence of a mutation in the BRCA1 coding sequence, comprising:
    (a) amplifying a DNA fragment of an individual's BRCA1 coding sequence using an oligonucleotide primer which specifically hybridizes to sequences within the gene;
    (b) sequencing said amplified DNA fragment by dideoxy sequencing;
    (c) repeating steps (a) and (b) until said individual's BRCA1 coding sequence is completely sequenced;
    (d) comparing the sequence of said amplified DNA fragment to a BRCA1$^{(omi)}$ DNA sequence, SEQ. ID. NO1, SEQ. ID. NO3, or SEQ. ID. NO5;
    (e) determining any sequence differences between said individual's BRCA1 coding sequences and SEQ. ID. NO1, SEQ. ID. NO3, or SEQ. ID. NO5; to determine the presence or absence of base changes in said individual's BRCA1 coding sequence wherein a base change which is not any one of the following:
        AGC and AGT at position 2201,
        TTG and CTG at position 2430,
        CCG and CTG at position 2731,
        GAA and GGA at position 3232,
        AAA and AGA at position 3667,
        TCT and TCC at position 4427, and
        AGT and GGT at position 4956 is correlated with the potential of increased genetic susceptibility to breast or ovarian cancer resulting from a BRCA1 mutation in the BRCA1 coding sequence.

20. A method of claim 19 wherein, codon variations occur at the following frequencies, respectively, in a population free of disease:
    at position 2201, AGC and AGT occur at frequencies from about 40%, and from about 55–65%, respectively;
    at position 2430, TTG and CTG occur at frequencies from about 35–45%, and from about 55–65%, respectively;
    at position 2731, CCG and CTG occur at frequencies from about 25–35%, and from about 65–75%, respectively;
    at position 3232, GAA and GGA occur at frequencies from about 35–45%, and from about 55–65%, respectively;
    at position 3667, AAA and AGA occur at frequencies from about 35–45%, and from about 55–65%, respectively;
    at position 4427, TCT and TCC occur at frequencies from about 45–55%, and from about 45–55%, respectively; and
    at position 4956, AGT and GGT occur at frequencies from about 35–45%, and from about 55–65%, respectively.

21. A method according to claim 19 wherein said oligonucleotide primer is labeled with a radiolabel, a fluorescent label a bioluminescent label, a chemiluminescent label, or an enzyme label.

22. A set of codon pairs, which occur at polymorphic positions in a BRCA1 gene with a BRCA1 coding sequence according to claim 1, wherein said set of codon pairs is:
    AGC and AGT at position 2201;
    TTG and CTG at position 2430;
    CCG and CTG at position 2731;
    GAA and GGA at position 3232;
    AAA and AGA at position 3667;
    TCT and TCC at position 4427; and
    AGT and GGT at position 4956.

23. A set of at least two alternative codon pairs according to claim 22 wherein set of at least two alternative codon pairs occur at the following frequencies:
    at position 2201, AGC and AGT occur at frequencies of about 40%, and from about 55–65%, respectively;
    at position 2430, TTG and CTG occur at frequencies from about 35–45%, and from about 55–65%, respectively;
    at position 2731, CCG and CTG occur at frequencies from about 25–35%, and from about 65–75%, respectively;
    at position 3232, GAA and GGA occur at frequencies from about 35–45%, and from about 55–65%, respectively;
    at position 3667, AAA and AGA occur at frequencies from about 35–45%, and from about 55–65%, respectively;
    at position 4427, TCT and TCC occur at frequencies from about 45–55%, and from about 45–55%, respectively; and
    at position 4956, AGT and GGT occur at frequencies from about 35–45%, and from about 55–65%, respectively.

24. A BRCA1 coding sequence according to claim 1 wherein the codon pairs occur at the following frequencies:
    at position 2201, AGC and AGT occur at frequencies of about 40%, and from about 55–65%, respectively;
    at position 2430, TTG and CTG occur at frequencies from about 35–45%, and from about 55–65%, respectively;
    at position 2731, CCG and CTG occur at frequencies from about 25–35%, and from about 65–75%, respectively;
    at position 3232, GAA and GGA occur at frequencies from about 35–45%, and from about 55–65%, respectively;
    at position 3667, AAA and AGA occur at frequencies from about 35–45%, and from about 55–65%, respectively;
    at position 4427, TCT and TCC occur at frequencies from about 45–55%, and from about 45–55%, respectively; and
    at position 4956, AGT and GGT occur at frequencies from about 35–45%, and from about 55–65%, respectively.

25. A method of determining the consensus genomic sequence or consensus coding sequence for a target gene, comprising:
    a) screening a number of individuals in a population for a family history which indicates inheritance of normal alleles for a target gene;
    b) isolating at least one allele of the target gene from individuals found to have a family history which indicates inheritance of normal alleles for a target gene;
    c) sequencing each allele;
    d) comparing the nucleic acid sequence of the genomic sequence or of the coding sequence of each allele of the target gene to determine similarities and differences in the nucleic acid sequence; and e) determining which allele of the target gene occurs with the greatest frequency.

26. A method of performing gene therapy, comprising:
    a) transfecting cancer cell in vivo with an effective amount of a vector transformed with a BRCA1 coding sequences of SEQ. ID. NO.: 1, SEQ. ID. NO.: 3, or SEQ. ID. NO.: 5;
    b) allowing the cells to take up the vector, and
    c) measuring a reduction in tumor growth.

27. A method of performing protein therapy, comprising:
    a) injecting into a patient, an effective amount of BRCA1 tumor growth inhibiting protein of SEQ. ID. NO.: 2, SEQ. ID. NO.: 4, or SEQ. ID. NO.: 6;
    b) allowing the cells to take up the protein, and
    c) measuring a reduction in tumor growth.

Sequencing

Any nucleic acid, specimen, in purified or non-purified form, can be utilized as the starting nucleic acid or acids, providing it contains, or is suspected of containing, the specific nucleic acid sequence containing a polymorphic locus. Thus, the process may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. See TABLE II. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from a body sample, such as blood, tissue material and the like by a variety of techniques such as that described by Maniatis, et. al. in *Molecular Cloning:A Laboratory Manual*, Cold Spring Harbor, N.Y., p 280–281, 1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The primers used to carry out this invention embrace oligonucleotides of sufficient length and appropriate sequence to provide initiation of polymerization. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers used to carry out this invention are designed to be substantially complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the mutation to hybridize therewith and permit amplification of the genomic locus.

Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859–1862, 1981. One method for synthesizing oligonucleotides on a modified solid support is described in U.S. Pat. No. 4,458,066.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (e.i., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. Amplification is described in *PCR, A Practical Approach*, ILR Press, Eds. M. J. McPherson, P. Quirke, and G. R. Taylor, 1992.

The amplification products may be detected by Southern blots analysis, without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et. al., *Bio/Technology*, 3:1008–1012, 1985), allele-specific oligonucleotide (ASO) probe analysis (Conner, et. al., *Proc. Natl. Acad. Sci. U.S.A.*, 80:278, 1983), oligonucleotide ligation assays (OLAs) (Landgren, et. al., *Science*, 241:1007, 1988), and the like. Molecular techniques for DNA analysis have been reviewed (Landgren, et. al., *Science*, 242:229–237, 1988).

Preferably, the method of amplifying is by PCR, as described herein and as is commonly used by those of ordinary skill in the art. Alternative methods of amplification have been described and can also be employed as long as the BRCA1 locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. Another amplification system useful in the method of the invention is the QB Replicase System. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking DNA repair. Nucleic acid amplification by strand displacement activation (SDA) utilizes a short primer containing a recognition site for hincII with short overhang on the 5' end which binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the cite of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented Temperature cycling.

Another method is a process for amplifying nucleic acid sequences from a DNA or RNA template which may be purified or may exist in a mixture of nucleic acids. The resulting nucleic acid sequences may be exact copies of the template, or may be modified. The process has advantages over PCR in that it increases the fidelity of copying a specific nucleic acid sequence, and it allows one to more efficiently detect a particular point mutation in a single assay. A target nucleic acid is amplified enzymatically while avoiding strand displacement. Three primers are used. A first primer is complementary to the first end of the target. A second primer is complementary to the second end of the target. A third primer which is similar to the first end of the target and which is substantially complementary to at least a portion of the first primer such that when the third primer is hybridized to the first primer, the position of the third primer complementary to the base at the 5' end of the first primer contains a modification which substantially avoids strand displacement. This method is detailed in U.S. Pat. No. 5,593,840 to Bhatnagar et al. 1997. Although PCR is the preferred method of amplification if the invention, these other methods can also be used to amplify the BRCA1 locus as described in the method of the invention.

The BRCA1$^{(omi)}$ DNA coding sequences were obtained by end to end sequencing of the BRCA1 alleles of five subjects in the manner described above followed by analysis of the data obtained. The data obtained provided us with the opportunity to evaluate seven previously published polymorphisms and to affirm or correct where necessary, the frequency of occurrence of alternative codons.

Gene Therapy

The coding sequences can be used for gene therapy.

A variety of methods are known for gene transfer, any of which might be available for use.

Direct Injection of Recombinant DNA in Vivo

1. Direct injection of "naked" DNA directly with a syringe and needle into a specific tissue, infused through a vascular bed, or transferred through a catheter into endothelial cells.

2. Direct injection of DNA that is contained in artificially generated lipid vesicles.

3. Direct injection of DNA conjugated to a targeting structure, such as an antibody.

4. Direct injection by particle bombardment, where the DNA is coated onto gold particles and shot into the cells.

Human Artificial Chromosomes

This novel gene delivery approach involves the use of human chromosomes that have been striped down to contain only the essential components for replication and the genes desired for transfer.

Receptor-Mediated Gene Transfer

DNA is linked to a targeting molecule that will bind to specific cell-surface receptors, inducing endocytosis and transfer of the DNA into mammalian cells. One such technique uses poly-L-lysine to link asialoglycoprotein to DNA. An adenovirus is also added to the complex to disrupt the lysosomes and thus allow the DNA to avoid degradation and move to the nucleus. Infusion of these particles intravenously has resulted in gene transfer into hepatocytes.

Recombinant Virus Vectors

Several vectors are used in gene therapy. Among them are the Moloney Murine Leukemia Virus (MoMLV) Vectors, the adenovirus vectors, the adeno-Associated Virus (AAV) vectors, the herpes simplex virus (HSV) vectors, the poxvirus vectors, and human immunodeficiency virus (HIV) vectors, Gene Replacement and Repair The ideal genetic manipulation for treatment of a genetic disease would be the actual replacement of the defective gene with a normal copy of the gene. Homologous recombination is the term used for switching out a section of DNA and replacing it with a new piece. By this technique, the defective gene can be replaced with a normal gene which expresses a functioning BRCA1 tumor growth inhibitor protein.

A complete description of gene therapy can also be found in "Gene Therapy A Primer For Physicians" 2d Ed. by Kenneth W. Culver, M.D. Publ. Mary Ann Liebert Inc. (1996). Two Gene Therapy Protocols for BRCA1 are approved by the Recombinant DNA Advisory Committee for Jeffrey T. Holt et al. They are listed as 9602-148, and 9603-149 and are available from the NIH. The isolated BRCA1 gene can be synthesized or constructed from amplification products and inserted into a vector such as the LXSN vector.

The BRCA1 amino acid and nucleic acid sequence may be used to make diagnostic probes and antibodies. Labeled diagnostic probes may be used by any hybridization method to determine the level of BRCA1 protein in serum or lysed cell suspension of a patient, or solid surface cell sample.

The BRCA1 amino acid sequence may be used to provide a level of protection for patients against risk of breast or ovarian cancer or to reduce the size of a tumor. Methods of making and extracting proteins are well known. Itakura et al. U.S. Pat. Nos. 4,704,362, 5,221,619, and 5,583,013. BRCA1 has been shown to be secreted. Jensen, R. A. et al. *Nature Genetics* 12: 303–308 (1996).

EXAMPLE 1

Determination of the Coding Sequence of a BRCA1$^{(omi)}$ Gene from Five Individuals Materials and Methods Approximately 150 volunteers were screened in order to identify individuals with no cancer history in their immediate family (i.e. first and second degree relatives). Each person was asked to fill out a hereditary cancer prescreening questionnaire See TABLE I below. Five of these were randomly chosen for end-to-end sequencing of their BRCA1 gene. A first degree relative is a parent, sibling, or offspring. A second degree relative is an aunt, uncle, grandparent, grandchild, niece, nephew, or half-sibling.

TABLE I

Hereditary Cancer Pre-Screening Questionnaire

Part A: Answer the following questions about your family

1. To your knowledge, has anyone in your family been diagnosed with a very specific hereditary colon disease called Familial Adenomatous Polyposis (FAP)?
2. To your knowledge, have you or any aunt had breast cancer diagnosed before the age 35?
3. Have you had Inflammatory Bowel Disease, also called Crohn's Disease or Ulcerative Colitis, for more than 7 years?

Part B: Refer to the list of cancers below for your responses only to questions in Part B

| Bladder Cancer | Lung Cancer | Pancreatic Cancer |
| Breast Cancer | Gastric Cancer | Prostate Cancer |
| Colon Cancer | Malignant Melanoma | Renal Cancer |
| Endometrial Cancer | Ovarian Cancer | Thyroid Cancer |

4. Have your mother or father, your sisters or brothers or your children had any of the listed cancers?
5. Have there been diagnosed in your mother's brothers or sisters, or your mother's parents more than one of the cancers in the above list?
6. Have there been diagnosed in your father's brothers or sisters, or your father's parents one of the cancers in the above List?

Part C: Refer to the list of relatives below for responses only to questions in Part C

| You | Your mother |
| Your sisters or brothers | Your mothers's sisters or brothers (maternal aunts and uncles) |
| Your children | Your mother's parents (maternal grandparents) |

7. Have there been diagnosed in these relatives 2 or more identical types of cancer? Do not count "simple" skin cancer, also called basal cell or squamous cell skin cancer.
8. Is there a total of 4 or more of any cancers in the list of relatives above other than "simple" skin cancers?

Part D: Refer to the list of relatives below for responses only to questions in Part D.

| You | Your father |
| Your sisters or brothers | Your fathers's sisters or brothers (paternal aunts and uncles) |
| Your children | Your father's parents (paternal grandparents) |

9. Have there been diagnosed in these relatives 2 or more identical types of cancer? Do not count "simple" skin cancer, also called basal cell or squamous cell skin cancer.
10. Is there a total of 4 or more of any cancers in the list of relatives above other than "simple" skin cancers?

Genomic DNA was isolated from white blood cells of five subjects selected from analysis of their answers to the questions above. Dideoxy sequence analysis was performed following polymerase chain reaction amplification.

All exons of the BRCA1 gene were subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye was attached for automated sequencing using the Taq Dye Terminator® Kit (Perkin-Elmer cat#401628). DNA sequencing was performed in both forward and reverse directions on an Applied Biosystems, Inc. (ABI) automated Model 377® sequencer. The software used for analysis of the resulting data was Sequence Navigator® software purchased through ABI.

1. Polymerase Chain Reaction (PCR) Amplification

Genomic DNA (100 nanograms) extracted from white blood cells of five subjects. Each of the five samples was sequenced end to end. Each sample was amplified in a final volume of 25 microliters containing 1 microliter (100 nanograms) genomic DNA, 2.5 microliters 10× PCR buffer (100 mM Tris, pH 8.3, 500 mM KCl, 1.2 mM $MgCl_2$), 2.5 microliters 13× dNTP mix (2 mM each nucleotide), 2.5 microliters forward primer, 2.5 microliters reverse primer, and 1 microliter Taq polymerase (5 units), and 13 microliters of water.

The primers in Table II, below were used to carry out amplification of the various sections of the BRCA1 gene samples. The primers were synthesized on an DNA/RNA Model 394® Synthesizer.

TABLE II

BRCA1 PRIMERS AND SEQUENCING DATA

| EXON | | SEQUENCE | SEQ. ID NO. | MER | Mg++ | SIZE |
|---|---|---|---|---|---|---|
| EXON 2 | 2F | 5' GAA GTT GTC ATT TTA TAA ACC TTT-3' | 7 | 24 | 1.6 | ~275 |
| | 2R | 5' TGT CTT TTC TTC CCT AGT ATG T-3 | 8 | 22 | | |
| EXON 3 | 3F | 5' TCC TGA CAC AGC AGA CAT TTA-3' | 9 | 21 | 1.4 | ~375 |
| | 3R | 5' TTG GAT TTT CGT TCT CAC TTA-3' | 10 | 21 | | |
| EXON 5 | 5F | 5' CTC TTA AGG GCA GTT GTG AG-3' | 11 | 20 | 1.2 | ~275 |
| | 5R | 5' TTC CTA CTG TGG TTG CTT CC | 12 | 20[1] | | |
| EXON 6 | 6/7F | 5' CTT ATT TTA GTG TCC TTA AAA GG-3' | 13 | 23 | 1.6 | ~250 |
| | 6R | 5' TTT CAT GGA CAG CAC TTTG AGT G-3' | 14 | 22 | | |
| EXON 7 | 7F | 5' CAC AAC AAA GAG CAT ACA TAG GG-3' | 15 | 23 | 1.6 | ~275 |
| | 6/7R | 5' TCG GGT TCA CTC TGT AGA AG-3' | 16 | 20 | | |
| EXON 8 | 8F1 | 5' TTC TCT TCA GGA GGA AAA GCA-3' | 17 | 21 | 1.2 | ~270 |
| | 8R1 | 5' GCT GCC TAC CAC AAA TAC AAA-3' | 18 | 21 | | |
| EXON 9 | 9F | 5' CCA CAG TAG ATG CTC AGT AAATA-3' | 19 | 23 | 1.2 | ~250 |
| | 9R | 5' TAG GAA AAT ACC AGC TTC ATA GA-3' | 20 | 23 | | |
| EXON 10 | 10F | 5' TGG TCA GCT TTC TGT AAT CG-3' | 21 | 20 | 1.6 | ~250 |
| | 10R | 5' GTA TCT ACC CAC TCT CTT CTT CAG-3' | 22 | 24 | | |
| EXON 11A | 11AF | 5' CCA CCT CCA AGG TGT ATC A-3' | 23 | 19 | 1.2 | 372 |
| | 11AR | 5' TGT TAT GTT GGC TCC TTG CT-3' | 24 | 20 | | |
| EXON 11B | 11BF1 | 5' CAC TAA AGA CAG AAT GAA TCT A-3' | 25 | 21 | 1.2 | ~400 |
| | 11BR1 | 5' GAA GAA CCA GAA TAT TCA TCT A-3' | 26 | 21 | | |
| EXON 11C | 11CF1 | 5' TGA TGG GGA GTC TGA ATC AA-3' | 27 | 20 | 1.2 | ~400 |
| | 11CR1 | 5' TCT GCT TTC TTG ATA AAA TCC T-3' | 28 | 22 | | |
| EXON 11D | 11DF1 | 5' AGC GTC CCC TCA CAA ATA AA-3' | 29 | 20 | 1.2 | ~400 |
| | 11DR1 | 5' TCA AGC GCA TGA ATA TGC CT-3' | 30 | 20 | | |
| EXON 11E | 11EF | 5' GTA TAA GCA ATA TGG AAC TCG A-3' | 31 | 22 | 1.2 | 388 |
| | 11ER | 5' TTA AGT TCA CTG GTA TTT GAA CA-3' | 32 | 23 | | |
| EXON 11F | 11FF | 5' GAC AGC GAT ACT TTC CCA GA-3' | 33 | 20 | 1.2 | 382 |
| | 11FR | 5' TGG AAC AAC CAT GAA TTA GTC-3' | 34 | 21 | | |
| EXON 11G | 11GF | 5' GGA AGT TAG CAC TCT AGG GA-3' | 35 | 20 | 1.2 | 423 |
| | 11GR | 5' GCA GTG ATA TTA ACT GTC TGT A-3' | 36 | 22 | | |
| EXON 11H | 11HF | 5' TGG GTC CTT AAA GAA ACA AAGT-3' | 37 | 22 | 1.2 | 366 |
| | 11HR | 5' TCA GGT GAC ATT GAA TCT TCC-3' | 38 | 21 | | |
| EXON 11I | 11IF | 5' CCA CTT TTT CCC ATC AAG TCA-3' | 39 | 21 | 1.2 | 377 |
| | 11IR | 5' TCA GGA TGC TTA CAA TTA CTT C-3' | 40 | 21 | | |
| EXON 11J | 11JF | 5' CAA AAT TGA ATG CTA TGC TTA GA-3' | 41 | 23 | 1.2 | 377 |
| | 11JR | 5' TCG GTA ACC TGA GCC AAA AT-3' | 42 | 20 | | |
| EXON 11K | 11KF | 5' GCA AAAGCGTCC AGA AAG GA-3' | 43 | 20 | 1.2 | 396 |
| | 11KR-1 | 5' TAT TTG CAG TCA AGT CTT CCA A-3' | 44 | 22 | | |
| EXON 11L | 11LF-1 | 5' GTA ATA TTG GCA AAG GCA TCT-3' | 45 | 22 | 1.2 | 360 |
| | 11LR | 5' TAA AAT GTG CTC CCC AAA AGC A-3' | 46 | 22 | | |
| EXON 12 | 12F | 5' GTC CTG CCA ATG AGA AGA AA-3' | 47 | 20 | 1.2 | ~300 |
| | 12R | 5' TGT CAG CAA ACC TAA GAA TGT-3' | 48 | 21 | | |

TABLE II-continued

BRCA1 PRIMERS AND SEQUENCING DATA

| EXON | | SEQUENCE | SEQ. ID NO. | MER | Mg++ | SIZE |
|---|---|---|---|---|---|---|
| EXON 13 | 13F | 5' AAT GGA AAG CTT CTC AAAGTA-3' | 49 | 21 | 1.2 | ~325 |
| | 13R | 5' ATG TTG GAG CTA GGT CCT TAC-3' | 50 | 21 | | |
| EXON 14 | 14F | 5' CTA ACC TGA ATT ATC ACT ATC A-3' | 51 | 22 | 1.2 | ~310 |
| | 14R | 5' GTG TAT AAATGC CTG TAT GCA-3' | 52 | 21 | | |
| EXON 15 | 15F | 5' TGG CTG CCC AGG AAG TAT G-3' | 53 | 19 | 1.2 | ~375 |
| | 15R | 5' AAC CAG AAT ATC TTT ATG TAG GA-3' | 54 | 23 | | |
| EXON 16 | 16F | 5' AAT TCT TAA CAG AGA CCA GAA C-3' | 55 | 22 | 1.6 | ~550 |
| | 16R | 5' AAA ACT CTT TCC AGA ATG TTG T-3' | 56 | 22 | | |
| EXON 17 | 17F | 5' GTG TAG AAC GTG CAG GAT TG-3' | 57 | 20 | 1.2 | ~275 |
| | 17R | 5' TCG CCT CAT GTG GTT TTA-3' | 58 | 18 | | |
| EXON 18 | 18F | 5' GGC TCT TTA GCT TCT TAG GAC-3' | 59 | 21 | 1.2 | ~350 |
| | 18R | 5' GAG ACC ATT TTC CCA GCA TC-3' | 60 | 20 | | |
| EXON 19 | 19F | 5' CTG TCA TTC TTC GTG TGC TC-3' | 61 | 20 | 1.2 | ~250 |
| | 19R | 5' CAT TGT TAA GGA AAG TGG TGC-3' | 62 | 21 | | |
| EXON 20 | 20F | 5' ATA TGA CGT GTC TGC TCC AC-3' | 63 | 20 | 1.2 | ~425 |
| | 20R | 5' GGG AAT CCA AAT TAC ACA GC-3' | 64 | 20 | | |
| EXON 21 | 21F | 5' AAG CTC TTC CTT TTT GAA AGT C-3' | 65 | 22 | 1.6 | ~300 |
| | 21R | 5' GTA GAG AAA TAG AAT AGC CTC T-3' | 66 | 22 | | |
| EXON 22 | 22F | 5' TCC CAT TGA GAG GTC TTG CT-3' | 67 | 20 | 1.6 | ~300 |
| | 22R | 5' GAG AAG ACT TCT GAG GCT AC-3' | 68 | 20 | | |
| EXON 23 | 23F-1 | 5' TGA AGT GAC AGT TCC AGT AGT-3' | 69 | 21 | 1.2 | ~250 |
| | 23R-1 | 5' CAT TTT AGC CAT TCA TTC AAC AA-3' | 70 | 23 | | |
| EXON 24 | 24F | 5' ATG AAT TGA CAC TAA TCT CTG C-3' | 71 | 22 | 1.4 | ~285 |
| | 24R | 5' GTA GCC AGG ACA GTA GAA GGA-3' | 72 | 21 | | |

[1] M13 tailed

Thirty-five cycles were performed, each consisting of denaturing (95° C.; 30 seconds), annealing (55° C.; 1 minute), and extension (72° C.; 90 seconds), except during the first cycle in which the denaturing time was increased to 5 minutes, and during the last cycle in which the extension time was increased to 5 minutes.

PCR products were purified using Qia-quick® PCR purification kits (Qiagen cat#28104; Chatsworth, Calif.). Yield and purity of the PCR product determined spectrophotometrically at $OD_{260}$ on a Beckman DU 650 spectrophotometer.

2. Dideoxy Sequence Analysis

Fluorescent dye was attached to PCR products for automated sequencing using the Taq Dye Terminator® Kit (Perkin-Elmer cat#401628). DNA sequencing was performed in both forward and reverse directions on an Applied Biosystems, Inc. (ABI) Foster City, Calif., automated Model 377® sequencer. The software used for analysis of the resulting data was "Sequence Navigator® software" purchased through ABI.

3. Results

Differences in the nucleic acids of the ten alleles from five individuals were found in seven locations on the gene. The changes and their positions are found on TABLE III, below.

TABLE III

| AMINO ACID CHANGE | NUCLEOTIDE CHANGE | PANEL TYPING | | | | | FREQUENCY |
|---|---|---|---|---|---|---|---|
| | | 1 | 2 | 3 | 4 | 5 | |
| SER (SER) (694) | 11E | C/C | C/T | C/T | T/T | T/T | 0.4 C 0.6 T |
| LEU (LEU) (771) | 11F | T/T | C/T | C/T | C/C | C/C | 0.4 T 0.6 C |
| PRO (LEU) (871) | 11G | C/T | C/T | C/T | T/T | T/T | 0.3 C 0.7 T |
| GLU (GLY) (1038) | 11I | A/A | A/G | A/G | G/G | G/G | 0.4 A 0.6 G |
| LYS (ARG) (1183) | 11J | A/A | A/G | A/G | G/G | G/G | 0.4 A 0.6 G |
| SER (SER) (1436) | 13 | T/T | T/T | T/C | C/C | C/C | 0.5 T 0.5 C |
| SER (GLY) (1613) | 16 | A/A | A/G | A/G | G/G | G/G | 0.4 A 0.6 G |

Tables 3 and 4 depict one aspect of the invention, sets of at least two alternative codon pairs wherein the codon pairs occur in the following frequencies, respectively, in a population of individuals free of disease:

at position 2201, AGC and AGT occur at frequencies from about 35–45%, and from about 55–65%, respectively;

at position 2430, TTG and CTG occur at frequencies from about 35–45%, and from about 55–65%, respectively;

at position 2731, CCG and CTG occur at frequencies from about 25–35%, and from about 65–75%, respectively;

at position 3232, GAA and GGA occur at frequencies from about 35–45%, and from about 55–65%, respectively;

at position 3667, AAA and AGA occur at frequencies from about 35–45%, and from about 55–65%, respectively;

at position 4427, TCT and TCC occur at frequencies from about 45–55%, and from about 45–55%, respectively; and at position 4956, AGT and GGT occur at frequencies from about 35–45%, and from about 55–65%, respectively.

The data show that for each of the samples. The BRCA1 gene is identical except in the region of seven polymorphisms. These polymorphic regions, together with their locations, the amino acid groups of each codon, the frequency of their occurrence and the amino acid coded for by each codon are found in TABLE IV below.

GAA and GGA at position 3232,
AAA and AGA at position 3667,
TCT and TCC at position 4427, and
AGT and GGT at position 4956.

The availability of these polymorphic pairs provides added assurance that one skilled in the art can correctly interpret the polymorphic variations without mistaking a variation for a mutation.

Exon 11 of the BRCA1 gene is subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye is attached for automated sequencing using the Taq Dye Terminator® Kit (Perkin-Elmer cat#401628). DNA sequencing is performed in both forward and reverse directions on an Applied Biosystems, Inc. (ABI) automated Model 377® sequencer. The software used for analysis of the resulting data is "Sequence Navigator® software" purchased through ABI.

1. Polymerase Chain Reaction (PCR) Amplification

Genomic DNA (100 nanograms) extracted from white blood cells of the subject is amplified in a final volume of 25 microliters containing 1 microliter (100 nanograms) genomic DNA, 2.5 microliters 10× PCR buffer (100 mM Tris, pH 8.3, 500 mM KCl, 1.2 mM $MgCl_2$), 2.5 microliters 10× dNTP mix (2 mM each nucleotide), 2.5 microliters

TABLE IV

CODON AND BASE CHANGES IN SEVEN POLYMORPHIC SITES OF BRCA1 GENE

| SAMPLE NAME | BASE CHANGE | POSITION nt/aa | EXON | CODON CHANGE | AA CHANGE | PUBLISHED FREQUENCY[2] | FREQUENCY IN THIS STUDY |
|---|---|---|---|---|---|---|---|
| 2,3,4,5 | C-T | 2201/694 | 11E | AGC(AGT) | SER-SER | UNPUBLISHED | C = 40% |
| 2,3,4,5 | T-C | 2430/771 | 11F | TTG(CTG) | LEU-LEU | T = 67%[13] | T = 40% |
| 1,2,3,4,5 | C-T | 2731/871 | 11G | CCG(CTG) | PRO-LEU | C = 34%[12] | C = 30% |
| 2,3,4,5 | A-G | 3232/1038 | 11I | GAA(GGA) | GLU-GLY | A = 67%[13] | A = 40% |
| 2,3,4,5 | A-G | 3667/1183 | 11J | AAA(AGA) | LYS-ARG | A = 68%[12] | A = 40% |
| 3,4,5 | T-C | 4427/1436 | 13 | TCT(TCC) | SER-SER | T = 67%[12] | T = 50% |
| 2,3,4,5 | A-G | 4956/1613 | 16 | AGT(GGT) | SER-GLY | A = 67%[12] | A = 40% |

[2]Reference numbers correspond to the Table of References below.

EXAMPLE 2

Determination of a Individual Using BRCA1$^{(OMI)}$ and the Seven Polymorphisms for Reference A person skilled in the art of genetic susceptibility testing will find the present invention useful for:

a) identifying individuals having a BRCA1 gene, who are therefore have no elevated genetic susceptibility to breast or ovarian cancer from a BRCA1 mutation;

b) avoiding misinterpretation of polymorphisms found in the BRCA1 gene;

Sequencing is carried out as in EXAMPLE 1 using a blood sample from the patient in question. However, a BRCA1$^{(omi)}$ sequence is used for reference and the polymorphic sites are compared to the nucleic acid sequences listed above for codons at each polymorphic site. A sample is one which compares to a BRCA1$^{(omi)}$ sequence and contains one of the base variations which occur at each of the polymorphic sites. The codons which occur at each of the polymorphic sites are paired here reference.

AGC and AGT at position 2201,
TTG and CTG at position 2430,
CCG and CTG at position 2731, forward primer (BRCA1-11K-F, 10 micromolar solution), 2.5 microliters reverse primer (BRCA1-11K-R, 10 micromolar solution), and 1 microliter Taq polymerase (5 units), and 13 microliters of water.

The PCR primers used to amplify a patient's sample BRCA1 gene are listed in Table II. The primers were synthesized on an DNA/RNA Model 394® Synthesizer. Thirty-five cycles are of amplification are performed, each consisting of denaturing (95° C.; 30 seconds), annealing (55° C.; 1 minute), and extension (72° C.; 90 seconds), except during the first cycle in which the denaturing time is increased to 5 minutes, and during the last cycle in which the extension time is increased to 5 minutes.

PCR products are purified using Qia-quick® PCR purification kits (Qiagen, cat#28104; Chatsworth, Calif.). Yield and purity of the PCR product determined spectrophotometrically at $OD_{260}$ on a Beckman DU 650 spectrophotometer.

2. Dideoxy Sequence Analysis

Fluorescent dye is attached to PCR products for automated sequencing using the Taq Dye Terminator® Kit (Perkin-Elmer cat#401628). DNA sequencing is performed in both forward and reverse directions on an Applied Biosystems, Inc. (ABI) Foster City, Calif., automated Model 377® sequencer. The software used for analysis of the resulting data is "Sequence Navigator® software" purchased through ABI. The BRCA1$^{(omi1)}$ SEQ. ID. NO.:1 sequence is entered into the Sequence Navigator® software as the Standard for comparison. The Sequence Navigator® software compares the sample sequence to the BRCA1$^{(omi1)}$ SEQ. ID. NO.:1 standard, base by base. The Sequence Navigator® software highlights all differences between the BRCA1$^{(omi1)}$ SEQ. ID. NO.:1 DNA sequence and the patient's sample sequence.

A first technologist checks the computerized results by comparing visually the BRCA1$^{(omi1)}$ SEQ. ID. NO.:1 standard against the patient's sample, and again highlights any differences between the standard and the sample. The first primary technologist then interprets the sequence variations at each position along the sequence. Chromatograms from each sequence variation are generated by the Sequence Navigator® software and printed on a color printer. The peaks are interpreted by the first primary technologist and a second primary technologist. A secondary technologist then reviews the chromatograms. The results are finally interpreted by a geneticist. In each instance, a variation is compared to known polymorphisms for position and base change. If the sample BRCA1 sequence matches the BRCA1$^{(omi1)}$ SEQ. ID. NO.:1 standard, with only variations within the known list of polymorphisms, it is interpreted as a gene sequence.

EXAMPLE 3
Determining the Absence of a Mutation in the BRCA1 Gene Using BRCA1$^{(omi1)}$ and Seven Polymorphisms for Reference A person skilled in the art of genetic susceptibility testing will find the present invention useful for determining the presence of a known or previously unknown mutation in the BRCA1 gene. A list of mutations of BRCA1 is publicly available at the Breast Cancer Information Core web site. This data site became publicly available on Nov. 1, 1995. Friend, S. et al. *Nature Genetics* 11:238, (1995).

Sequencing is carried out as in EXAMPLE 1 using a blood sample from the patient in question. However, a BRCA1$^{(omi)}$ sequence is used for reference and polymorphic sites are compared to the nucleic acid sequences listed above for codons at each polymorphic site. A sample is one which compares to the BRCA1 $^{(omi2)}$ SEQ. ID. NO.: 3 sequence and contains one of the base variations which occur at each of the polymorphic sites. The codons which occur at each of the polymorphic sites are paired here reference.

AGC and AGT at position 2201,

TTG and CTG at position 2430,

CCG and CTG at position 2731,

GAA and GGA at position 3232,

AAA and AGA at position 3667,

TCT and TCC at position 4427, and

AGT and GGT at position 4956.

The availability of these polymorphic pairs provides added assurance that one skilled in the art can correctly interpret the polymorphic variations without mistaking a variation for a mutation.

Exon 11 of the BRCA1 gene is subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye is attached for automated sequencing using the Taq Dye Terminator® Kit (Perkin-Elmer cat#401628). DNA sequencing is performed in both forward and reverse directions on an Applied Biosystems, Inc. (ABI) automated Model 377® sequencer. The software used for analysis of the resulting data is "Sequence Navigator® software" purchased through ABI.

1. Polymerase Chain Reaction (PCR) Amplification

Genomic DNA (100 nanograms) extracted from white blood cells of the subject is amplified in a final volume of 25 microliters containing 1 microliter (100 nanograms) genomic DNA, 2.5 microliters 10× PCR buffer (100 mM Tris, pH 8.3, 500 mM KCl, 1.2 mM $MgCl_2$), 2.5 microliters 10× dNTP mix (2 mM each nucleotide), 2.5 microliters forward primer (BRCA1–11K-F, 10 micromolar solution), 2.5 microliters reverse primer (BRCA1–11K-R, 10 micromolar solution), and 1 microliter Taq polymerase (5 units), and 13 microliters of water.

The PCR primers used to amplify a patient's sample BRCA1 gene are listed in Table II. The primers were synthesized on an DNA/RNA Model 394® Synthesizer. Thirty-five cycles are of amplification are performed, each consisting of denaturing (95° C.; 30 seconds), annealing (55° C.; 1 minute), and extension (72° C.; 90 seconds), except during the first cycle in which the denaturing time is increased to 5 minutes, and during the last cycle in which the extension time is increased to 5 minutes.

PCR products are purified using Qia-quick® PCR purification kits (Qiagen, cat#28104; Chatsworth, Calif.). Yield and purity of the PCR product determined spectrophotometrically at $OD_{260}$ on a Beckman DU 650 spectrophotometer.

2. Dideoxy Sequence Analysis

Fluorescent dye is attached to PCR products for automated sequencing using the Taq Dye Terminator® Kit (Perkin-Elmer cat#401628). DNA sequencing is performed in both forward and reverse directions on an Applied Biosystems, Inc. (ABI) Foster City, Calif., automated Model 377® sequencer. The software used for analysis of the resulting data is "Sequence Navigator® software" purchased through ABI. The BRCA1$^{(omi2)}$ SEQ. ID. NO.: 3 sequence is entered into the Sequence Navigator® software as the Standard for comparison. The Sequence Navigator® software compares the sample sequence to the BRCA1$^{(omi2)}$ SEQ. ID. NO.: 3 standard, base by base. The Sequence Navigator® software highlights all differences between the BRCA1$^{(omi2)}$ SEQ. ID. NO.: 3 DNA sequence and the patient's sample sequence.

A first technologist checks the computerized results by comparing visually the BRCA1$^{(omi2)}$ SEQ. ID. NO.: 3 standard against the patient's sample, and again highlights any differences between the standard and the sample. The first primary technologist then interprets the sequence variations at each position along the sequence. Chromatograms from each sequence variation are generated by the Sequence Navigator® software and printed on a color printer. The peaks are interpreted by the first primary technologist and also by a second primary technologist. A secondary technologist then reviews the chromatograms. The results are finally interpreted by a geneticist. In each instance, a variation is compared to known polymorphisms for position and base change. If the sample BRCA1 sequence matches the BRCA1$^{(omi2)}$ SEQ. ID. NO.: 3 standard, with only variations within the known list of polymorphisms, it is interpreted as a gene sequence.

EXAMPLE 4
Determining the Presence of a Mutation in the BRCA1 Gene Using BRCA1$^{(omi)}$ and Seven Polymorphisms for Reference A person skilled in the art of genetic susceptibility testing will find the present invention useful for determining the presence of a known or previously unknown mutation in the BRCA1 gene. A list of mutations of BRCA1 is publicly available at the Breast Cancer Information Core website. This data site became publicly available on Nov. 1, 1995. Friend, S. et al. *Nature Genetics* 11:238, (1995). In this example, a mutation in exon 11 is characterized by amplifying the region of the mutation with a primer which matches the region of the mutation.

Exon 11 of the BRCA1 gene is subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye is attached for automated sequencing using the Taq Dye Terminator® Kit (Perkin-Elmer cat#401628). DNA sequencing is performed in both forward and reverse directions on an Applied Biosystems, Inc. (ABI) automated Model 377® sequencer. The software used for analysis of the resulting data is "Sequence Navigator® software" purchased through ABI.

1. Polymerase Chain Reaction (PCR) Amplification

Genomic DNA (100 nanograms) extracted from white blood cells of the subject is amplified in a final volume of 25 microliters containing 1 microliter (100 nanograms) genomic DNA, 2.5 microliters 10× PCR buffer (100 mM Tris, pH 8.3, 500 mM KCl, 1.2 mM $MgCl_2$), 2.5 microliters 10× dNTP mix (2 mM each nucleotide), 2.5 microliters forward primer (BRCA1–11K-F, 10 micromolar solution), 2.5 microliters reverse primer (BRCA1–11K-R, 10 micromolar solution),and 1 microliter Taq polymerase (5 units), and 13 microliters of water.

The PCR primers used to amplify segment K of exon 11 (where the mutation is found) are as follows:
BRCA1–11K-F: 5'-GCA AAA GCG TCC AGA AAG GA-3' SEQ ID NO:69
BRCA1–11K-R: 5'-AGT CTT CCA ATT CAC TGC AC-3' SEQ ID NO:70

The primers are synthesized on an DNA/RNA Model 394® Synthesizer.

Thirty-five cycles are performed, each consisting of denaturing (95° C.; 30 seconds), annealing (55° C.; 1 minute), and extension (72° C.; 90 seconds), except during the first cycle in which the denaturing time is increased to 5 minutes, and during the last cycle in which the extension time is increased to 5 minutes.

PCR products are purified using Qia-quick® PCR purification kits (Qiagen, cat#28104; Chatsworth, Calif.). Yield and purity of the PCR product determined spectrophotometrically at $OD_{260}$ on a Beckman DU 650 spectrophotometer.

2. Dideoxy Sequence Analysis

Fluorescent dye is attached to PCR products for automated sequencing using the, Taq Dye Terminators Kit (Perkin-Elmer cat#401628). DNA sequencing is performed in both forward and reverse directions on an Applied Biosystems, Inc. (ABI) Foster City, Calif., automated Model 377® sequencer. The software used for analysis of the resulting data is "Sequence Navigator® software" purchased through ABI. The BRCA1$^{(omi2)}$ SEQ. ID. NO.: 3 sequence is entered into the Sequence Navigator® software as the Standard for comparison. The Sequence Navigator® software compares the sample sequence to the BRCA1$^{(omi2)}$ SEQ. ID. NO.: 3 standard, base by base. The Sequence Navigator® software highlights all differences between the BRCA1$^{(omi2)}$ SEQ. ID. NO.: 3 DNA sequence and the patient's sample sequence.

A first technologist checks the computerized results by comparing visually the BRCA1$^{(omi2)}$ SEQ. ID. NO.: 3 standard against the patient's sample, and again highlights any differences between the standard and the sample. The first primary technologist then interprets the sequence variations at each position along the sequence. Chromatograms from each sequence variation are generated by the Sequence Navigator® software and printed on a color printer. The peaks are interpreted by the first primary technologist and a second primary technologist. A secondary technologist then reviews the chromatograms. The results are finally interpreted by a geneticist. In each instance, a variation is compared to known polymorphisms for position and base change. Mutations are noted by the length of non-matching variation. Such a lengthy mismatch pattern occurs with deletions and substitutions.

3. Result

Using the above PCR amplification and standard fluorescent sequencing technology, The 3888delGA mutation may be found. The 3888delGA mutation The BRCA1 gene lies in segment "K" of exon 11. The DNA sequence results demonstrate the presence of a two base pair deletion at nucleotides 3888 and 3889 of the published BRCA1$^{(omi)}$ sequence. This mutation interrupts the reading frame of the BRCA1 transcript, resulting in the appearance of an in-frame terminator (TAG) at codon position 1265. This mutation is, therefore, predicted to result in a truncated, and most likely, non-functional protein. The formal name of the mutation will be 3888delGA. This mutation is named in accordance with the suggested nomenclature for naming mutations, Baudet, A et al., *Human Mutation* 2:245–248, (1993).

EXAMPLE 5
Use of the BRCA1$^{(omi1)}$ Gene Therapy

The growth of ovarian, breast or prostate cancer can be arrested by increasing the expression of the BRCA1 gene where inadequate expression of that gene is responsible for hereditary ovarian, breast and prostate cancer. It has been demonstrated that transfection of BRCA1 into cancer cells inhibits their growth and reduces tumorigenesis. Gene therapy is performed on a patient to reduce the size of a tumor. The LXSN vector is transformed with any of the BRCA1$^{(omi1)}$ SEQ. ID. NO.:1, BRCA1$^{(omi2)}$ SEQ. ID. NO.:3, or BRCA1$^{(omi3)}$ SEQ. ID. NO.:5 coding region.
Vector The LXSN vector is transformed with wildtype BRCA1$^{(omi1)}$ SEQ. ID. NO.:1 coding sequence. The LXSN-BRCA1$^{(omi1)}$ retroviral expression vector is constructed by cloning a SalI-linkered BRCA1$^{(omi1)}$ cDNA (nucleotides 1–5711) into the XhoI site of the vector LXSN. Constructs are confirmed by DNA sequencing. Holt et al. *Nature Genetics* 12: 298–302 (1996). Retroviral vectors are manufactured from viral producer cells using serum free and phenol-red free conditions and tested for sterility, absence of specific pathogens, and absence of replication-competent retrovirus by standard assays. Retrovirus is stored frozen in aliquots which have been tested.

Patients receive a complete physical exam, blood, and urine tests to determine overall health. They may also have a chest X-ray, electrocardiogram, and appropriate radiologic procedures to assess tumor stage.

Patients with metastatic ovarian cancer are treated with retroviral gene therapy by infusion of recombinant LXSN-BRCA1$^{(omi1)}$ retroviral vectors into peritoneal sites containing tumor, between $10^9$ and $10^{10}$ viral particles per dose.

Blood samples are drawn each day and tested for the presence of retroviral vector by sensitive polymerase chain reaction (PCR)-based assays. The fluid which is removed is analyzed to determine:

1. The percentage of cancer cells which are taking up the recombinant LXSN-BRCA1$^{(omi1)}$ retroviral vector combination. Successful transfer of BRCA1 gene into cancer cells is shown by both RT-PCR analysis and in situ hybridization. RT-PCR is performed with by the method of Thompson et al. *Nature Genetics* 9: 444–450 (1995), using primers derived from BRCA1$^{(omi1)}$ SEQ. ID. NO.:1. Cell lysates are prepared and immunoblotting is performed by the method of Jensen et al. *Nature Genetics* 12: 303–308 1996) and Jensen et al. *Biochemistry* 31: 10887–10892 (1992).

2. Presence of programmed cell death using ApoTAG® in situ apoptosis detection kit (Oncor, Inc., Gaithersburg, Md.) and DNA analysis.

3. Measurement of BRCA1 gene expression by slide immunofluorescence or western blot.

Patients with measurable disease are also evaluated for a clinical response to LXSN-BRCA1, especially those that do not undergo a palliative intervention immediately after retroviral vector therapy. Fluid cytology, abdominal girth, CT scans of the abdomen, and local symptoms are followed. For other sites of disease, conventional response criteria are used as follows:

1. Complete Response (CR), complete disappearance of all measurable lesions and of all signs and symptoms of disease for at least 4 weeks.
2. Partial Response (PR), decrease of at least 50% of the sum of the products of the 2 largest perpendicular diameters of all measurable lesions as determined by 2 observations not less than 4 weeks apart. To be considered a PR, no new lesions should have appeared during this period and none should have increased in size.
3. Stable Disease, less than 25% change in tumor volume from previous evaluations.
4. Progressive Disease, greater than 25% increase in tumor measurements from prior evaluations.

The number of doses depends upon the response to treatment.

For further information related to this gene therapy approach see in "BRCA1 Retroviral Gene Therapy for Ovarian Cancer" a Human Gene Transfer Protocol: NIH ORDA Registration #: 9603-149 Jeffrey Holt, J T, M.D. and Carlos L. Arteaga, M.D.

TABLE OF REFERENCES

1. Sanger, F., et al., *J. Mol. Biol.* 42:1617, (1980).
2. Beaucage, et al., *Tetrahedron Letters* 22:1859–1862, (1981).
3. Maniatis, et. al. in *Molecular Cloning:A Laboratory Manual*, Cold Spring Harbor, N.Y., p 280–281, (1982).
4. Conner, et. al., *Proc. Natl. Acad. Sci.* U.S.A. 80:278, (1983)
5. Saiki, et. al., *Bio/Technology* 3:1008–1012, (1985)
6. Landgren, et. al., *Science* 241:1007, (1988)
7. Landgren, et. al., *Science* 242 :229–237, (1988).
8. PCR. A Practical Approach, ILR Press, Eds. M. J. McPherson, P. Quirke, and G. R. Taylor, (1992).
9. Easton et al., *American Journal of Human Genetics* 52:678–701, (1993).
10. U.S. Pat. No. 4,458,066.
11. Rowell, S., et al., *American Journal of Human Genetics* 55:861–865, (1994)
12. Miki, Y. et al., *Science* 266:66–71, (1994).
13. Friedman, L. et al., *Nature Genetics* 8:399–404, (1994).
14. Baudet, A et al., *Human Mutation* 2:245–248, (1993).
15. Friend, S. et al., *Nature Genetics* 11:238, (1995).
16. Arteaga, C L and J T Holt *Cancer Research* 56:1098–1103 (1996).
17. Holt, J T et al., *Nature Genetics* 12:298–302 (1996).
18. Jensen, R A et al., *Nature Genetics* 12:303–308 (1996).
19. Steeg, P. *Nature Genetics* 12:223–225 (1996).
20. Thompson, M E et al., *Nature Genetics* 9: 444–450 (1995)
21. Holt, J T, and C. Arteaga, Gene Therapy Protocol ORDA #: 9603-149 ORDA approved Protocol for BRCA1 Gene Therapy.

"Breast and Ovarian cancer" is understood by those skilled in the art to include breast and ovarian cancer in women and also breast and prostate cancer in men. BRCA1 is associated genetic susceptibility to inherited breast and ovarian cancer in women and also breast and prostate cancer in men. Therefore, claims in this document which recite breast and/or ovarian cancer refer to breast, ovarian and prostate cancers in men and women. Although the invention has been described with reference to the presently preferred embodiments, it should be understood that various modifications can be made without departing from the spirit of the invention. Accordingly, the invention is limited only by the following claims.

What is claimed is:

1. An isolated nucleic acid molecule comprising the nucleotide sequence of SEQ ID NO: 3.

2. The isolated nucleic acid molecule of claim 1, wherein the nucleic acid consists essentially of the nucleotide sequence of SEQ ID NO: 3.

3. The isolated nucleic acid molecule of claim 1, wherein the nucleic acid molecule consists of the nucleotide sequence of SEQ ID NO: 3.

4. The isolated nucleic acid molecule of claim 1, wherein the nucleic acid molecule comprises nucleotides 120 to 5,708 of SEQ ID NO: 3.

5. The isolated nucleic acid molecule of claim 1, wherein the nucleic acid molecule consists of nucleotides 120 to 5,708 of SEQ ID NO: 3.

6. The isolated nucleic acid molecule of claim 1, wherein the nucleic acid molecule is operably linked to one or more expression control elements.

7. A vector comprising an isolated nucleic acid molecule of claim 1.

8. A host cell comprising the vector of claim 7.

9. A host cell transformed to contain the nucleic acid molecule of claim 1.

10. A host cell of claim 8 or 9, wherein said host is selected from the group consisting of prokaryotic hosts and eukaryotic hosts.

11. A method for producing a polypeptide comprising culturing a host cell of claim 8 or 9 under in vitro conditions in which the protein encoded by the nucleic acid molecule is expressed.

12. A method for producing a polypeptide comprising culturing a host cell containing a nucleic acid comprising the nucleotide sequence of SEQ ID NO: 3 under in vitro conditions in which the protein encoded by the nucleic acid molecule is expressed.

13. The method of claim 12, wherein the nucleic acid consists essentially of the nucleotide sequence of SEQ ID NO: 3.

14. The method of claim 12, wherein the nucleic acid molecule consists of the nucleotide sequence of SEQ ID NO: 3.

15. The method of claim 12, wherein the nucleic acid molecule comprises nucleotides 120 to 5,708 of SEQ ID NO: 3.

16. The method of claim 12, wherein the nucleic acid molecule consists of nucleotides 120 to 5,708 of SEQ ID NO: 3.

* * * * *

SEQUENCE LISTING (1) GENERAL INFORMATION:

(iii) NUMBER OF SEQUENCES: 72

(2) INFORMATION FOR SEQ ID NO: 1:

(i) SEQUENCE CHARACTERISTICS:
      (A) LENGTH: 5711 base pairs
      (B) TYPE: nucleic acid
      (C) STRANDEDNESS: Not Relevant
      (D) TOPOLOGY: linear (ii) MOLECULE TYPE: cDNA (vi) ORIGINAL SOURCE:
    (A) ORGANISM: Homo sapiens
    (B) STRAIN: BRCA1

(viii) POSITION IN GENOME:
    (A) CHROMOSOME/SEGMENT: 17
    (B) MAP POSITION: 17q21

(xi) SEQUENCE DESCRIPTION: SEQ ID NO: 1:

```
AGCTCGCTGA GACTTCCTGG ACCCCGCACC AGGCTGTGGG GTTTCTCAGA TAACTGGGCC      60
CCTGCGCTCA GGAGGCCTTC ACCCTCTGCT CTGGGTAAAG TTCATTGGAA CAGAAAGAAA     120
TGGATTTATC TGCTCTTCGC GTTGAAGAAG TACAAAATGT CATTAATGCT ATGCAGAAAA     180
TCTTAGAGTG TCCCATCTGT CTGGAGTTGA TCAAGGAACC TGTCTCCACA AAGTGTGACC     240
ACATATTTTG CAAATTTTGC ATGCTGAAAC TTCTCAACCA GAAGAAAGGG CCTTCACAGT     300
GTCCTTTATG TAAGAATGAT ATAACCAAAA GGAGCCTACA AGAAAGTACG AGATTTAGTC     360
AACTTGTTGA AGAGCTATTG AAAATCATTT GTGCTTTTCA GCTTGACACA GGTTTGGAGT     420
ATGCAAACAG CTATAATTTT GCAAAAAAGG AAAATAACTC TCCTGAACAT CTAAAAGATG     480
AAGTTTCTAT CATCCAAAGT ATGGGCTACA GAAACCGTGC CAAAAGACTT CTACAGAGTG     540
AACCCGAAAA TCCTTCCTTG CAGGAAACCA GTCTCAGTGT CCAACTCTCT AACCTTGGAA     600
CTGTGAGAAC TCTGAGGACA AAGCAGCGGA TACAACCTCA AAAGACGTCT GTCTACATTG     660
AATTGGGATC TGATTCTTCT GAAGATACCG TTAATAAGGC AACTTATTGC AGTGTGGGAG     720
ATCAAGAATT GTTACAAATC ACCCCTCAAG GAACCAGGGA TGAAATCAGT TTGGATTCTG     780
CAAAAAAGGC TGCTTGTGAA TTTTCTGAGA CGGATGTAAC AAATACTGAA CATCATCAAC     840
CCAGTAATAA TGATTTGAAC ACCACTGAGA AGCGTGCAGC TGAGAGGCAT CCAGAAAAGT     900
ATCAGGGTAG TTCTGTTTCA AACTTGCATG TGGAGCCATG TGGCACAAAT ACTCATGCCA     960
GCTCATTACA GCATGAGAAC AGCAGTTTAT TACTCACTAA AGACAGAATG AATGTAGAAA    1020
AGGCTGAATT CTGTAATAAA AGCAAACAGC CTGGCTTAGC AAGGAGCCAA CATAACAGAT    1080
GGGCTGGAAG TAAGGAAACA TGTAATGATA GGCGGACTCC CAGCACAGAA AAAAAGGTAG    1140
ATCTGAATGC TGATCCCCTG TGTGAGAGAA AGAATGGAAT AAGCAGAAA CTGCCATGCT    1200
CAGAGAATCC TAGAGATACT GAAGATGTTC CTTGGATAAC ACTAAATAGC AGCATTCAGA    1260
AAGTTAATGA GTGGTTTTCC AGAAGTGATG AACTGTTAGG TTCTGATGAC TCACATGATG    1320
GGGAGTCTGA ATCAAATGCC AAAGTAGCTG ATGTATTGGA CGTTCTAAAT GAGGTAGATG    1380
AATATTCTGG TTCTTCAGAG AAAATAGACT TACTGGCCAG TGATCCTCAT GAGGCTTTAA    1440
TATGTAAAAG TGAAAGAGTT CACTCCAAAT CAGTAGAGAG TAATATTGAA GACAAAATAT    1500
TTGGGAAAAC CTATCGGAAG AAGGCAAGCC TCCCCAACTT AAGCCATGTA ACTGAAAATC    1560
TAATTATAGG AGCATTTGTT ACTGAGCCAC AGATAATACA AGAGCGTCCC CTCACAAATA    1620
AATTAAAGCG TAAAAGGAGA CCTACATCAG GCCTTCATCC TGAGGATTTT ATCAAGAAAG    1680
CAGATTTGGC AGTTCAAAAG ACTCCTGAAA TGATAAATCA GGGAACTAAC CAAACGGAGC    1740
AGAATGGTCA AGTGATGAAT ATTACTAATA GTGGTCATGA GAATAAAACA AAAGGTGATT    1800
CTATTCAGAA TGAGAAAAAT CCTAACCCAA TAGAATCACT CGAAAAAGAA TCTGCTTTCA    1860
AAACGAAAGC TGAACCTATA AGCAGCAGTA TAAGCAATAT GGAACTCGAA TTAAATATCC    1920
ACAATTCAAA AGCACCTAAA AAGAATAGGC TGAGGAGGAA GTCTTCTACC AGGCATATTC    1980
ATGCGCTTGA ACTAGTAGTC AGTAGAAATC TAAGCCCACC TAATTGTACT GAATTGCAAA    2040
TTGATAGTTG TTCTAGCAGT GAAGAGATAA AGAAAAAAAA GTACAACCAA ATGCCAGTCA    2100
```

```
GGCACAGCAG AAACCTACAA CTCATGGAAG GTAAAGAACC TGCAACTGGA GCCAAGAAGA    2160

GTAACAAGCC AAATGAACAG ACAAGTAAAA GACATGACAG TGATACTTTC CCAGAGCTGA    2220

AGTTAACAAA TGCACCTGGT TCTTTTACTA AGTGTTCAAA TACCAGTGAA CTTAAAGAAT    2280

TTGTCAATCC TAGCCTTCCA AGAGAAGAAA AAGAAGAGAA ACTAGAAACA GTTAAAGTGT    2340

CTAATAATGC TGAAGACCCC AAAGATCTCA TGTTAAGTGG AGAAAGGGTT TTGCAAACTG    2400

AAAGATCTGT AGAGAGTAGC AGTATTTCAC TGGTACCTGG TACTGATTAT GGCACTCAGG    2460

AAAGTATCTC GTTACTGGAA GTTAGCACTC TAGGGAAGGC AAAAACAGAA CCAAATAAAT    2520

GTGTGAGTCA GTGTGCAGCA TTTGAAAACC CCAAGGGACT AATTCATGGT TGTTCCAAAG    2580

ATAATAGAAA TGCACAGAA GGCTTTAAGT ATCCATTGGG ACATGAAGTT AACCACAGTC    2640

GGGAAACAAG CATAGAAATG GAAGAAAGTG AACTTGATGC TCAGTATTTG CAGAATACAT    2700

TCAAGGTTTC AAAGCGCCAG TCATTTGCTC TGTTTTCAAA TCCAGGAAAT GCAGAAGAGG    2760

AATGTGCAAC ATTCTCTGCC CACTCTGGGT CCTTAAAGAA ACAAAGTCCA AAAGTCACTT    2820

TTGAATGTGA ACAAAAGGAA GAAAATCAAG GAAAGAATGA GTCTAATATC AAGCCTGTAC    2880

AGACAGTTAA TATCACTGCA GGCTTTCCTG TGGTTGGTCA GAAAGATAAG CCAGTTGATA    2940

ATGCCAAATG TAGTATCAAA GGAGGCTCTA GGTTTTGTCT ATCATCTCAG TTCAGAGGCA    3000

ACGAAACTGG ACTCATTACT CCAAATAAAC ATGGACTTTT ACAAAACCCA TATCGTATAC    3060

CACCACTTTT TCCCATCAAG TCATTTGTTA AAACTAAATG TAAGAAAAAT CTGCTAGAGG    3120

AAAACTTTGA GGAACATTCA ATGTCACCTG AAAGAGAAAT GGGAAATGAG AACATTCCAA    3180

GTACAGTGAG CACAATTAGC CGTAATAACA TTAGAGAAAA TGTTTTTAAA GGAGCCAGCT    3240

CAAGCAATAT TAATGAAGTA GGTTCCAGTA CTAATGAAGT GGGCTCCAGT ATTAATGAAA    3300

TAGGTTCCAG TGATGAAAAC ATTCAAGCAG AACTAGGTAG AAACAGAGGG CCAAAATTGA    3360

ATGCTATGCT TAGATTAGGG GTTTTGCAAC CTGAGGTCTA TAAACAAAGT CTTCCTGGAA    3420

GTAATTGTAA GCATCCTGAA ATAAAAAAGC AAGAATATGA AGAAGTAGTT CAGACTGTTA    3480

ATACAGATTT CTCTCCATAT CTGATTTCAG ATAACTTAGA ACAGCCTATG GGAAGTAGTC    3540

ATGCATCTCA GGTTTGTTCT GAGACACCTG ATGACCTGTT AGATGATGGT GAAATAAAGG    3600

AAGATACTAG TTTTGCTGAA AATGACATTA AGGAAAGTTC TGCTGTTTTT AGCAAAAGCG    3660

TCCAGAGAGG AGAGCTTAGC AGGAGTCCTA GCCCTTTCAC CCATACACAT TTGGCTCAGG    3720

GTTACCGAAG AGGGGCCAAG AAATTAGAGT CCTCAGAAGA GAACTTATCT AGTGAGGATG    3780

AAGAGCTTCC CTGCTTCCAA CACTTGTTAT TTGGTAAAGT AAACAATATA CCTTCTCAGT    3840

CTACTAGGCA TAGCACCGTT GCTACCGAGT GTCTGTCTAA GAACACAGAG GAGAATTTAT    3900

TATCATTGAA GAATAGCTTA AATGACTGCA GTAACCAGGT AATATTGGCA AAGGCATCTC    3960

AGGAACATCA CCTTAGTGAG GAAACAAAAT GTTCTGCTAG CTTGTTTTCT TCACAGTGCA    4020

GTGAATTGGA AGACTTGACT GCAAATACAA ACACCCAGGA TCCTTTCTTG ATTGGTTCTT    4080

CCAAACAAAT GAGGCATCAG TCTGAAAGCC AGGGAGTTGG TCTGAGTGAC AAGGAATTGG    4140

TTTCAGATGA TGAAGAAAGA GGAACGGGCT TGGAAGAAAA TAATCAAGAA GAGCAAAGCA    4200

TGGATTCAAA CTTAGGTGAA GCAGCATCTG GGTGTGAGAG TGAAACAAGC GTCTCTGAAG    4260

ACTGCTCAGG GCTATCCTCT CAGAGTGACA TTTTAACCAC TCAGCAGAGG GATACCATGC    4320

AACATAACCT GATAAAGCTC CAGCAGGAAA TGGCTGAACT AGAAGCTGTG TTAGAACAGC    4380

ATGGGAGCCA GCCTTCTAAC AGCTACCCTT CCATCATAAG TGACTCCTCT GCCCTTGAGG    4440
```

-continued

```
ACCTGCGAAA TCCAGAACAA AGCACATCAG AAAAAGCAGT ATTAACTTCA CAGAAAAGTA    4500

GTGAATACCC TATAAGCCAG AATCCAGAAG GCCTTTCTGC TGACAAGTTT GAGGTGTCTG    4560

CAGATAGTTC TACCAGTAAA AATAAAGAAC CAGGAGTGGA AAGGTCATCC CCTTCTAAAT    4620

GCCCATCATT AGATGATAGG TGGTACATGC ACAGTTGCTC TGGGAGTCTT CAGAATAGAA    4680

ACTACCCATC TCAAGAGGAG CTCATTAAGG TTGTTGATGT GGAGGAGCAA CAGCTGGAAG    4740

AGTCTGGGCC ACACGATTTG ACGGAAACAT CTTACTTGCC AAGGCAAGAT CTAGAGGGAA    4800

CCCCTTACCT GGAATCTGGA ATCAGCCTCT TCTCTGATGA CCCTGAATCT GATCCTTCTG    4860

AAGACAGAGC CCCAGAGTCA GCTCGTGTTG CAACATACC ATCTTCAACC TCTGCATTGA     4920

AAGTTCCCCA ATTGAAAGTT GCAGAATCTG CCCAGGGTCC AGCTGCTGCT CATACTACTG    4980

ATACTGCTGG GTATAATGCA ATGGAAGAAA GTGTGAGCAG GGAGAAGCCA GAATTGACAG    5040

CTTCAACAGA AAGGGTCAAC AAAAGAATGT CCATGGTGGT GTCTGGCCTG ACCCCAGAAG    5100

AATTTATGCT CGTGTACAAG TTTGCCAGAA AACACCACAT CACTTAACT AATCTAATTA     5160

CTGAAGAGAC TACTCATGTT GTTATGAAAA CAGATGCTGA GTTTGTGTGT GAACGGACAC    5220

TGAAATATTT TCTAGGAATT GCGGGAGGAA AATGGGTAGT TAGCTATTTC TGGGTGACCC    5280

AGTCTATTAA AGAAAGAAAA ATGCTGAATG AGCATGATTT TGAAGTCAGA GGAGATGTGG    5340

TCAATGGAAG AAACCACCAA GGTCCAAAGC GAGCAAGAGA ATCCCAGGAC AGAAAGATCT    5400

TCAGGGGGCT AGAAATCTGT TGCTATGGGC CCTTCACCAA CATGCCCACA GATCAACTGG    5460

AATGGATGGT ACAGCTGTGT GGTGCTTCTG TGGTGAAGGA GCTTTCATCA TTCACCCTTG    5520

GCACAGGTGT CCACCCAATT GTGGTTGTGC AGCCAGATGC CTGGACAGAG GACAATGGCT    5580

TCCATGCAAT TGGGCAGATG TGTGAGGCAC CTGTGGTGAC CCGAGAGTGG GTGTTGGACA    5640

GTGTAGCACT CTACCAGTGC CAGGAGCTGG ACACCTACCT GATACCCCAG ATCCCCCACA    5700

GCCACTACTG A                                                        5711
```

(2) INFORMATION FOR SEQ ID NO: 2:

(i) SEQUENCE CHARACTERISTICS:
        (A) LENGTH: 1863 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Homo sapiens
        (B) STRAIN: BRCA1

(viii) POSITION IN GENOME:
        (A) CHROMOSOME/SEGMENT: 17
        (B) MAP POSITION: 17q21

(xi) SEQUENCE DESCRIPTION: SEQ ID NO: 2:

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80
```

```
Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Ser Ser Glu Asp Thr Val Asn
            180                 185                 190

Lys Ala Thr Tyr Cys Ser Val Gly Asp Gln Glu Leu Leu Gln Ile Thr
            195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
            275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
            355                 360                 365

Asp Val Pro Trp Ile Thr Leu Asn Ser Ser Ile Gln Lys Val Asn Glu
    370                 375                 380

Trp Phe Ser Arg Ser Asp Glu Leu Leu Gly Ser Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Glu Arg Val His
            435                 440                 445

Ser Lys Ser Val Glu Ser Asn Ile Glu Asp Lys Ile Phe Gly Lys Thr
    450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495
```

-continued

```
Pro Leu Thr Asn Lys Leu Lys Arg Lys Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Glu Gln Asn Gly Gln
        530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ile Ser
            580                 585                 590

Asn Met Glu Leu Glu Leu Asn Ile His Asn Ser Lys Ala Pro Lys Lys
            595                 600                 605

Asn Arg Leu Arg Arg Lys Ser Ser Thr Arg His Ile His Ala Leu Glu
        610                 615                 620

Leu Val Val Ser Arg Asn Leu Ser Pro Pro Asn Cys Thr Glu Leu Gln
625                 630                 635                 640

Ile Asp Ser Cys Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
        690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
    850                 855                 860

Lys Arg Gln Ser Phe Ala Leu Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
```

-continued

```
                915                 920                 925
Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val Ser
    1010                1015                1020

Thr Ile Ser Arg Asn Asn Ile Arg Glu Asn Val Phe Lys Gly Ala Ser
1025                1030                1035                1040

Ser Ser Asn Ile Asn Glu Val Gly Ser Ser Thr Asn Glu Val Gly Ser
                1045                1050                1055

Ser Ile Asn Glu Ile Gly Ser Ser Asp Glu Asn Ile Gln Ala Glu Leu
            1060                1065                1070

Gly Arg Asn Arg Gly Pro Lys Leu Asn Ala Met Leu Arg Leu Gly Val
        1075                1080                1085

Leu Gln Pro Glu Val Tyr Lys Gln Ser Leu Pro Gly Ser Asn Cys Lys
    1090                1095                1100

His Pro Glu Ile Lys Lys Gln Glu Tyr Glu Glu Val Val Gln Thr Val
1105                1110                1115                1120

Asn Thr Asp Phe Ser Pro Tyr Leu Ile Ser Asp Asn Leu Glu Gln Pro
                1125                1130                1135

Met Gly Ser Ser His Ala Ser Gln Val Cys Ser Glu Thr Pro Asp Asp
            1140                1145                1150

Leu Leu Asp Asp Gly Glu Ile Lys Glu Asp Thr Ser Phe Ala Glu Asn
        1155                1160                1165

Asp Ile Lys Glu Ser Ser Ala Val Phe Ser Lys Ser Val Gln Arg Gly
    1170                1175                1180

Glu Leu Ser Arg Ser Pro Ser Pro Phe Thr His Thr His Leu Ala Gln
1185                1190                1195                1200

Gly Tyr Arg Arg Gly Ala Lys Lys Leu Glu Ser Ser Glu Glu Asn Leu
                1205                1210                1215

Ser Ser Glu Asp Glu Glu Leu Pro Cys Phe Gln His Leu Leu Phe Gly
            1220                1225                1230

Lys Val Asn Asn Ile Pro Ser Gln Ser Thr Arg His Ser Thr Val Ala
        1235                1240                1245

Thr Glu Cys Leu Ser Lys Asn Thr Glu Glu Asn Leu Leu Ser Leu Lys
    1250                1255                1260

Asn Ser Leu Asn Asp Cys Ser Asn Gln Val Ile Leu Ala Lys Ala Ser
1265                1270                1275                1280

Gln Glu His His Leu Ser Glu Glu Thr Lys Cys Ser Ala Ser Leu Phe
                1285                1290                1295

Ser Ser Gln Cys Ser Glu Leu Glu Asp Leu Thr Ala Asn Thr Asn Thr
            1300                1305                1310

Gln Asp Pro Phe Leu Ile Gly Ser Ser Lys Gln Met Arg His Gln Ser
        1315                1320                1325

Glu Ser Gln Gly Val Gly Leu Ser Asp Lys Glu Leu Val Ser Asp Asp
    1330                1335                1340
```

```
Glu Glu Arg Gly Thr Gly Leu Glu Asn Asn Gln Glu Gln Ser
1345                1350                1355                1360

Met Asp Ser Asn Leu Gly Glu Ala Ala Ser Gly Cys Glu Ser Glu Thr
                1365                1370                1375

Ser Val Ser Glu Asp Cys Ser Gly Leu Ser Ser Gln Ser Asp Ile Leu
            1380                1385                1390

Thr Thr Gln Gln Arg Asp Thr Met Gln His Asn Leu Ile Lys Leu Gln
        1395                1400                1405

Gln Glu Met Ala Glu Leu Glu Ala Val Leu Glu Gln His Gly Ser Gln
    1410                1415                1420

Pro Ser Asn Ser Tyr Pro Ser Ile Ile Ser Asp Ser Ser Ala Leu Glu
1425                1430                1435                1440

Asp Leu Arg Asn Pro Glu Gln Ser Thr Ser Glu Lys Ala Val Leu Thr
                1445                1450                1455

Ser Gln Lys Ser Ser Glu Tyr Pro Ile Ser Gln Asn Pro Glu Gly Leu
            1460                1465                1470

Ser Ala Asp Lys Phe Glu Val Ser Ala Asp Ser Ser Thr Ser Lys Asn
        1475                1480                1485

Lys Glu Pro Gly Val Glu Arg Ser Ser Pro Ser Lys Cys Pro Ser Leu
    1490                1495                1500

Asp Asp Arg Trp Tyr Met His Ser Cys Ser Gly Ser Leu Gln Asn Arg
1505                1510                1515                1520

Asn Tyr Pro Ser Gln Glu Glu Leu Ile Lys Val Val Asp Val Glu Glu
                1525                1530                1535

Gln Gln Leu Glu Glu Ser Gly Pro His Asp Leu Thr Glu Thr Ser Tyr
            1540                1545                1550

Leu Pro Arg Gln Asp Leu Glu Gly Thr Pro Tyr Leu Glu Ser Gly Ile
        1555                1560                1565

Ser Leu Phe Ser Asp Asp Pro Glu Ser Asp Pro Ser Glu Asp Arg Ala
    1570                1575                1580

Pro Glu Ser Ala Arg Val Gly Asn Ile Pro Ser Ser Thr Ser Ala Leu
1585                1590                1595                1600

Lys Val Pro Gln Leu Lys Val Ala Glu Ser Ala Gln Gly Pro Ala Ala
                1605                1610                1615

Ala His Thr Thr Asp Thr Ala Gly Tyr Asn Ala Met Glu Glu Ser Val
            1620                1625                1630

Ser Arg Glu Lys Pro Glu Leu Thr Ala Ser Thr Glu Arg Val Asn Lys
        1635                1640                1645

Arg Met Ser Met Val Val Ser Gly Leu Thr Pro Glu Glu Phe Met Leu
    1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
                1685                1690                1695

Cys Glu Arg Thr Leu Lys Tyr Phe Leu Gly Ile Ala Gly Gly Lys Trp
            1700                1705                1710

Val Val Ser Tyr Phe Trp Val Thr Gln Ser Ile Lys Glu Arg Lys Met
        1715                1720                1725

Leu Asn Glu His Asp Phe Glu Val Arg Gly Asp Val Val Asn Gly Arg
    1730                1735                1740

Asn His Gln Gly Pro Lys Arg Ala Arg Glu Ser Gln Asp Arg Lys Ile
1745                1750                1755                1760
```

```
Phe Arg Gly Leu Glu Ile Cys Cys Tyr Gly Pro Phe Thr Asn Met Pro
              1765                1770                1775

Thr Asp Gln Leu Glu Trp Met Val Gln Leu Cys Gly Ala Ser Val Val
          1780                1785                1790

Lys Glu Leu Ser Ser Phe Thr Leu Gly Thr Gly Val His Pro Ile Val
      1795                1800                1805

Val Val Gln Pro Asp Ala Trp Thr Glu Asp Asn Gly Phe His Ala Ile
      1810                1815                1820

Gly Gln Met Cys Glu Ala Pro Val Val Thr Arg Glu Trp Val Leu Asp
1825            1830                1835                1840

Ser Val Ala Leu Tyr Gln Cys Gln Glu Leu Asp Thr Tyr Leu Ile Pro
              1845                1850                1855

Gln Ile Pro His Ser His Tyr
          1860

(2) INFORMATION FOR SEQ ID NO: 3:

(i) SEQUENCE CHARACTERISTICS:
        (A) LENGTH: 5711 base pairs
        (B) TYPE: nucleic acid
        (C) STRANDEDNESS: Not Relevant
        (D) TOPOLOGY: linear (ii) MOLECULE TYPE: cDNA (vi) ORIGINAL SOURCE:
        (A) ORGANISM: Homo sapiens
        (B) STRAIN: BRCA1

(viii) POSITION IN GENOME:
        (A) CHROMOSOME/SEGMENT: 17
        (B) MAP POSITION: 17q21

(xi) SEQUENCE DESCRIPTION: SEQ ID NO: 3:

AGCTCGCTGA GACTTCCTGG ACCCCGCACC AGGCTGTGGG GTTTCTCAGA TAACTGGGCC      60

CCTGCGCTCA GGAGGCCTTC ACCCTCTGCT CTGGGTAAAG TTCATTGGAA CAGAAAGAAC     120

TGGATTTATC TGCTCTTCGC GTTGAAGAAG TACAAAATGT CATTAATGCT ATGCAGAAAA     180

TCTTAGAGTG TCCCATCTGT CTGGAGTTGA TCAAGGAACC TGTCTCCACA AAGTGTGACC     240

ACATATTTTG CAAATTTTGC ATGCTGAAAC TTCTCAACCA GAAGAAAGGG CCTTCACAGT     300

GTCCTTTATG TAAGAATGAT ATAACCAAAA GGAGCCTACA AGAAAGTACG AGATTTAGTC     360

AACTTGTTGA AGAGCTATTG AAAATCATTT GTGCTTTTCA GCTTGACACA GGTTTGGAGT     420

ATGCAAACAG CTATAATTTT GCAAAAAAGG AAAATAACTC TCCTGAACAT CTAAAAGATG     480

AAGTTTCTAT CATCCAAAGT ATGGGCTACA GAAACCGTGC CAAAAGACTT CTACAGAGTG     540

AACCCGAAAA TCCTTCCTTG CAGGAAACCA GTCTCAGTGT CCAACTCTCT AACCTTGGAA     600

CTGTGAGAAC TCTGAGGACA AAGCAGCGGA TACAACCTCA AAAGACGTCT GTCTACATTG     660

AATTGGGATC TGATTCTTCT GAAGATACCG TTAATAAGGC AACTTATTGC AGTGTGGGAG     720

ATCAAGAATT GTTACAAATC ACCCCTCAAG GAACCAGGGA TGAAATCAGT TTGGATTCTG     780

CAAAAAAGGC TGCTTGTGAA TTTTCTGAGA CGGATGTAAC AAATACTGAA CATCATCAAC     840

CCAGTAATAA TGATTTGAAC ACCACTGAGA AGCGTGCAGC TGAGAGGCAT CCAGAAAAGT     900

ATCAGGGTAG TTCTGTTTCA AACTTGCATG TGGAGCCATG TGGCACAAAT ACTCATGCCA     960

GCTCATTACA GCATGAGAAC AGCAGTTTAT TACTCACTAA AGACAGAATG AATGTAGAAA    1020

AGGCTGAATT CTGTAATAAA AGCAAACAGC CTGGCTTAGC AAGGAGCCAA CATAACAGAT    1080

GGGCTGGAAG TAAGGAAACA TGTAATGATA GGCGGACTCC CAGCACAGAA AAAAAGGTAG    1140
```

```
ATCTGAATGC TGATCCCCTG TGTGAGAGAA AAGAATGGAA TAAGCAGAAA CTGCCATGCT    1200

CAGAGAATCC TAGAGATACT GAAGATGTTC CTTGGATAAC ACTAAATAGC AGCATTCAGA    1260

AAGTTAATGA GTGGTTTTCC AGAAGTGATG AACTGTTAGG TTCTGATGAC TCACATGATG    1320

GGGAGTCTGA ATCAAATGCC AAAGTAGCTG ATGTATTGGA CGTTCTAAAT GAGGTAGATG    1380

AATATTCTGG TTCTTCAGAG AAAATAGACT TACTGGCCAG TGATCCTCAT GAGGCTTTAA    1440

TATGTAAAAG TGAAAGAGTT CACTCCAAAT CAGTAGAGAG TAATATTGAA GACAAAATAT    1500

TTGGGAAAAC CTATCGGAAG AAGGCAAGCC TCCCCAACTT AAGCCATGTA ACTGAAAATC    1560

TAATTATAGG AGCATTTGTT ACTGAGCCAC AGATAATACA AGAGCGTCCC CTCACAAATA    1620

AATTAAAGCG TAAAAGGAGA CCTACATCAG GCCTTCATCC TGAGGATTTT ATCAAGAAAG    1680

CAGATTTGGC AGTTCAAAAG ACTCCTGAAA TGATAAATCA GGGAACTAAC CAAACGGAGC    1740

AGAATGGTCA AGTGATGAAT ATTACTAATA GTGGTCATGA GAATAAAACA AAAGGTGATT    1800

CTATTCAGAA TGAGAAAAAT CCTAACCCAA TAGAATCACT CGAAAAGAA TCTGCTTTCA    1860

AAACGAAAGC TGAACCTATA AGCAGCAGTA TAAGCAATAT GGAACTCGAA TTAAATATCC    1920

ACAATTCAAA AGCACCTAAA AAGAATAGGC TGAGGAGGAA GTCTTCTACC AGGCATATTC    1980

ATGCGCTTGA ACTAGTAGTC AGTAGAAATC TAAGCCCACC TAATTGTACT GAATTGCAAA    2040

TTGATAGTTG TTCTAGCAGT GAAGAGATAA AGAAAAAAAA GTACAACCAA ATGCCAGTCA    2100

GGCACAGCAG AAACCTACAA CTCATGGAAG GTAAAGAACC TGCAACTGGA GCCAAGAAGA    2160

GTAACAAGCC AAATGAACAG ACAAGTAAAA GACATGACAG CGATACTTTC CCAGAGCTGA    2220

AGTTAACAAA TGCACCTGGT TCTTTTACTA AGTGTTCAAA TACCAGTGAA CTTAAAGAAT    2280

TTGTCAATCC TAGCCTTCCA AGAGAAGAAA AAGAAGAGAA ACTAGAAACA GTTAAAGTGT    2340

CTAATAATGC TGAAGACCCC AAAGATCTCA TGTTAAGTGG AGAAAGGGTT TTGCAAACTG    2400

AAAGATCTGT AGAGAGTAGC AGTATTTCAT TGGTACCTGG TACTGATTAT GGCACTCAGG    2460

AAAGTATCTC GTTACTGGAA GTTAGCACTC TAGGGAAGGC AAAAACAGAA CCAAATAAAT    2520

GTGTGAGTCA GTGTGCAGCA TTTGAAAACC CCAAGGGACT AATTCATGGT TGTTCCAAAG    2580

ATAATAGAAA TGACACAGAA GGCTTTAAGT ATCCATTGGG ACATGAAGTT AACCACAGTC    2640

GGGAAACAAG CATAGAAATG GAAGAAAGTG AACTTGATGC TCAGTATTTG CAGAATACAT    2700

TCAAGGTTTC AAAGCGCCAG TCATTTGCTC TGTTTTCAAA TCCAGGAAAT GCAGAAGAGG    2760

AATGTGCAAC ATTCTCTGCC CACTCTGGGT CCTTAAAGAA ACAAAGTCCA AAAGTCACTT    2820

TTGAATGTGA ACAAAAGGAA GAAAATCAAG GAAAGAATGA GTCTAATATC AAGCCTGTAC    2880

AGACAGTTAA TATCACTGCA GGCTTTCCTG TGGTTGGTCA GAAAGATAAG CCAGTTGATA    2940

ATGCCAAATG TAGTATCAAA GGAGGCTCTA GGTTTTGTCT ATCATCTCAG TTCAGAGGCA    3000

ACGAAACTGG ACTCATTACT CCAAATAAAC ATGGACTTTT ACAAAACCA TATCGTATAC    3060

CACCACTTTT TCCCATCAAG TCATTTGTTA AAACTAAATG TAAGAAAAAT CTGCTAGAGG    3120

AAAACTTTGA GGAACATTCA ATGTCACCTG AAAGAGAAAT GGGAAATGAG AACATTCCAA    3180

GTACAGTGAG CACAATTAGC CGTAATAACA TTAGAGAAAA TGTTTTTAAA GAAGCCAGCT    3240

CAAGCAATAT TAATGAAGTA GGTTCCAGTA CTAATGAAGT GGGCTCCAGT ATTAATGAAA    3300

TAGGTTCCAG TGATGAAAAC ATTCAAGCAG AACTAGGTAG AAACAGAGGG CCAAAATTGA    3360

ATGCTATGCT TAGATTAGGG GTTTTGCAAC CTGAGGTCTA TAAACAAAGT CTTCCTGGAA    3420

GTAATTGTAA GCATCCTGAA ATAAAAAAGC AAGAATATGA AGAAGTAGTT CAGACTGTTA    3480
```

-continued

```
ATACAGATTT CTCTCCATAT CTGATTTCAG ATAACTTAGA ACAGCCTATG GGAAGTAGTA      3540

ATGCATCTCA GGTTTGTTCT GAGACACCTG ATGACCTGTT AGATGATGGT GAAATAAAGG      3600

AAGATACTAG TTTTGCTGAA AATGACATTA AGGAAAGTTC TGCTGTTTTT AGCAAAAGCG      3660

TCCAGAAAGG AGAGCTTAGC AGGAGTCCTA GCCCTTTCAC CCATACACAT TTGGCTCAGG      3720

GTTACCGAAG AGGGGCCAAG AAATTAGAGT CCTCAGAAGA GAACTTATCT AGTGAGGATG      3780

AAGAGCTTCC CTGCTTCCAA CACTTGTTAT TTGGTAAAGT AAACAATATA CCTTCTCAGT      3840

CTACTAGGCA TAGCACCGTT GCTACCGAGT GTCTGTCTAA GAACACAGAG GAGAATTTAT      3900

TATCATTGAA GAATAGCTTA AATGACTGCA GTAACCAGGT AATATTGGCA AAGGCATCTC      3960

AGGAACATCA CCTTAGTGAG GAAACAAAAT GTTCTGCTAG CTTGTTTTCT TCACAGTGCA      4020

GTGAATTGGA AGACTTGACT GCAAATACAA ACACCCAGGA TCCTTTCTTG ATTGGTTCTT      4080

CCAAACAAAT GAGGCATCAG TCTGAAAGCC AGGGAGTTGG TCTGAGTGAC AAGGAATTGG      4140

TTTCAGATGA TGAAGAAAGA GGAACGGGCT TGGAAGAAAA TAATCAAGAA GAGCAAAGCA      4200

TGGATTCAAA CTTAGGTGAA GCAGCATCTG GGTGTGAGAG TGAAACAAGC GTCTCTGAAG      4260

ACTGCTCAGG GCTATCCTCT CAGAGTGACA TTTTAACCAC TCAGCAGAGG GATACCATGC      4320

AACATAACCT GATAAAGCTC CAGCAGGAAA TGGCTGAACT AGAAGCTGTG TTAGAACAGC      4380

ATGGGAGCCA GCCTTCTAAC AGCTACCCTT CCATCATAAG TGACTCTTCT GCCCTTGAGG      4440

ACCTGCGAAA TCCAGAACAA AGCACATCAG AAAAAGCAGT ATTAACTTCA CAGAAAGTA       4500

GTGAATACCC TATAAGCCAG AATCCAGAAG GCCTTTCTGC TGACAAGTTT GAGGTGTCTG      4560

CAGATAGTTC TACCAGTAAA AATAAAGAAC CAGGAGTGGA AAGGTCATCC CCTTCTAAAT      4620

GCCCATCATT AGATGATAGG TGGTACATGC ACAGTTGCTC TGGGAGTCTT CAGAATAGAA      4680

ACTACCCATC TCAAGAGGAG CTCATTAAGG TTGTTGATGT GGAGGAGCAA CAGCTGGAAG      4740

AGTCTGGGCC ACACGATTTG ACGGAAACAT CTTACTTGCC AAGGCAAGAT CTAGAGGGAA      4800

CCCCTTACCT GGAATCTGGA ATCAGCCTCT TCTCTGATGA CCCTGAATCT GATCCTTCTG      4860

AAGACAGAGC CCCAGAGTCA GCTCGTGTTG GCAACATACC ATCTTCAACC TCTGCATTGA      4920

AAGTTCCCCA ATTGAAAGTT GCAGAATCTG CCCAGAGTCC AGCTGCTGCT CATACTACTG      4980

ATACTGCTGG GTATAATGCA ATGGAAGAAA GTGTGAGCAG GGAGAAGCCA GAATTGACAG      5040

CTTCAACAGA AAGGGTCAAC AAAAGAATGT CCATGGTGGT GTCTGGCCTG ACCCCAGAAG      5100

AATTTATGCT CGTGTACAAG TTTGCCAGAA AACACCACAT CACTTTAACT AATCTAATTA      5160

CTGAAGAGAC TACTCATGTT GTTATGAAAA CAGATGCTGA GTTTGTGTGT GAACGGACAC      5220

TGAAATATTT TCTAGGAATT GCGGGAGGAA AATGGGTAGT TAGCTATTTC TGGGTGACCC      5280

AGTCTATTAA AGAAAGAAAA ATGCTGAATG AGCATGATTT TGAAGTCAGA GGAGATGTGG      5340

TCAATGGAAG AAACCACCAA GGTCCAAAGC GAGCAAGAGA ATCCCAGGAC AGAAAGATCT      5400

TCAGGGGGCT AGAAATCTGT TGCTATGGGC CCTTCACCAA CATGCCCACA GATCAACTGG      5460

AATGGATGGT ACAGCTGTGT GGTGCTTCTG TGGTGAAGGA GCTTTCATCA TTCACCCTTG      5520

GCACAGGTGT CCACCCAATT GTGGTTGTGC AGCCAGATGC CTGGACAGAG GACAATGGCT      5580

TCCATGCAAT TGGGCAGATG TGTGAGGCAC CTGTGGTGAC CCGAGAGTGG GTGTTGGACA      5640

GTGTAGCACT CTACCAGTGC CAGGAGCTGG ACACCTACCT GATACCCCAG ATCCCCCACA      5700

GCCACTACTG A                                                          5711
```

(2) INFORMATION FOR SEQ ID NO: 4:

-continued

```
    (i) SEQUENCE CHARACTERISTICS:
        (A) LENGTH: 1863 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Homo sapiens
        (B) STRAIN: BRCA1

(viii) POSITION IN GENOME:
        (A) CHROMOSOME/SEGMENT: 17
        (B) MAP POSITION: 17q21

(xi) SEQUENCE DESCRIPTION: SEQ ID NO: 4:

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
            85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
            115                 120                 125

Gly Tyr Arg Asn Arg Ala Lys Arg Leu Leu Gln Ser Glu Pro Glu Asn
            130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
            165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
            195                 200                 205

Pro Gln Gly Thr Arg Asp Glu Ile Ser Leu Asp Ser Ala Lys Lys Ala
210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
            245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
            275                 280                 285

Ser Leu Leu Leu Thr Lys Asp Arg Met Asn Val Glu Lys Ala Glu Phe
290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
```

-continued

```
                325                 330                 335
Glu Lys Lys Val Asp Leu Asn Ala Asp Pro Leu Cys Glu Arg Lys Glu
            340                 345                 350
Trp Asn Lys Gln Lys Leu Pro Cys Ser Glu Asn Pro Arg Asp Thr Glu
            355                 360                 365
Asp Val Pro Trp Ile Thr Leu Asn Ser Ser Ile Gln Lys Val Asn Glu
        370                 375                 380
Trp Phe Ser Arg Ser Asp Glu Leu Leu Gly Ser Asp Asp Ser His Asp
385                 390                 395                 400
Gly Glu Ser Glu Ser Asn Ala Lys Val Ala Asp Val Leu Asp Val Leu
                405                 410                 415
Asn Glu Val Asp Glu Tyr Ser Gly Ser Ser Glu Lys Ile Asp Leu Leu
            420                 425                 430
Ala Ser Asp Pro His Glu Ala Leu Ile Cys Lys Ser Glu Arg Val His
        435                 440                 445
Ser Lys Ser Val Glu Ser Asn Ile Glu Asp Lys Ile Phe Gly Lys Thr
    450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Ile Gln Glu Arg
                485                 490                 495
Pro Leu Thr Asn Lys Leu Lys Arg Lys Arg Arg Pro Thr Ser Gly Leu
            500                 505                 510
His Pro Glu Asp Phe Ile Lys Lys Ala Asp Leu Ala Val Gln Lys Thr
        515                 520                 525
Pro Glu Met Ile Asn Gln Gly Thr Asn Gln Thr Glu Gln Asn Gly Gln
    530                 535                 540
Val Met Asn Ile Thr Asn Ser Gly His Glu Asn Lys Thr Lys Gly Asp
545                 550                 555                 560
Ser Ile Gln Asn Glu Lys Asn Pro Asn Pro Ile Glu Ser Leu Glu Lys
                565                 570                 575
Glu Ser Ala Phe Lys Thr Lys Ala Glu Pro Ile Ser Ser Ser Ile Ser
            580                 585                 590
Asn Met Glu Leu Glu Leu Asn Ile His Asn Ser Lys Ala Pro Lys Lys
        595                 600                 605
Asn Arg Leu Arg Arg Lys Ser Ser Thr Arg His Ile His Ala Leu Glu
    610                 615                 620
Leu Val Val Ser Arg Asn Leu Ser Pro Pro Asn Cys Thr Glu Leu Gln
625                 630                 635                 640
Ile Asp Ser Cys Ser Ser Ser Glu Glu Ile Lys Lys Lys Lys Tyr Asn
                645                 650                 655
Gln Met Pro Val Arg His Ser Arg Asn Leu Gln Leu Met Glu Gly Lys
            660                 665                 670
Glu Pro Ala Thr Gly Ala Lys Lys Ser Asn Lys Pro Asn Glu Gln Thr
        675                 680                 685
Ser Lys Arg His Asp Ser Asp Thr Phe Pro Glu Leu Lys Leu Thr Asn
    690                 695                 700
Ala Pro Gly Ser Phe Thr Lys Cys Ser Asn Thr Ser Glu Leu Lys Glu
705                 710                 715                 720
Phe Val Asn Pro Ser Leu Pro Arg Glu Glu Lys Glu Glu Lys Leu Glu
                725                 730                 735
Thr Val Lys Val Ser Asn Asn Ala Glu Asp Pro Lys Asp Leu Met Leu
            740                 745                 750
```

```
Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
        770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                    805                 810                 815

Gly Cys Ser Lys Asp Asn Arg Asn Asp Thr Glu Gly Phe Lys Tyr Pro
                820                 825                 830

Leu Gly His Glu Val Asn His Ser Arg Glu Thr Ser Ile Glu Met Glu
            835                 840                 845

Glu Ser Glu Leu Asp Ala Gln Tyr Leu Gln Asn Thr Phe Lys Val Ser
        850                 855                 860

Lys Arg Gln Ser Phe Ala Leu Phe Ser Asn Pro Gly Asn Ala Glu Glu
865                 870                 875                 880

Glu Cys Ala Thr Phe Ser Ala His Ser Gly Ser Leu Lys Lys Gln Ser
                    885                 890                 895

Pro Lys Val Thr Phe Glu Cys Glu Gln Lys Glu Glu Asn Gln Gly Lys
                900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
        930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                    965                 970                 975

Pro Tyr Arg Ile Pro Pro Leu Phe Pro Ile Lys Ser Phe Val Lys Thr
                980                 985                 990

Lys Cys Lys Lys Asn Leu Leu Glu Glu Asn Phe Glu Glu His Ser Met
            995                 1000                1005

Ser Pro Glu Arg Glu Met Gly Asn Glu Asn Ile Pro Ser Thr Val Ser
        1010                1015                1020

Thr Ile Ser Arg Asn Asn Ile Arg Glu Asn Val Phe Lys Glu Ala Ser
1025                1030                1035                1040

Ser Ser Asn Ile Asn Glu Val Gly Ser Ser Thr Asn Glu Val Gly Ser
                    1045                1050                1055

Ser Ile Asn Glu Ile Gly Ser Ser Asp Glu Asn Ile Gln Ala Glu Leu
                1060                1065                1070

Gly Arg Asn Arg Gly Pro Lys Leu Asn Ala Met Leu Arg Leu Gly Val
            1075                1080                1085

Leu Gln Pro Glu Val Tyr Lys Gln Ser Leu Pro Gly Ser Asn Cys Lys
        1090                1095                1100

His Pro Glu Ile Lys Lys Gln Glu Tyr Glu Glu Val Val Gln Thr Val
1105                1110                1115                1120

Asn Thr Asp Phe Ser Pro Tyr Leu Ile Ser Asp Asn Leu Glu Gln Pro
                    1125                1130                1135

Met Gly Ser Ser His Ala Ser Gln Val Cys Ser Glu Thr Pro Asp Asp
                1140                1145                1150

Leu Leu Asp Asp Gly Glu Ile Lys Glu Asp Thr Ser Phe Ala Glu Asn
            1155                1160                1165
```

-continued

```
Asp Ile Lys Glu Ser Ser Ala Val Phe Ser Lys Ser Val Gln Lys Gly
    1170                1175                1180
Glu Leu Ser Arg Ser Pro Ser Pro Phe Thr His Thr His Leu Ala Gln
1185                1190                1195                1200
Gly Tyr Arg Arg Gly Ala Lys Lys Leu Glu Ser Ser Glu Glu Asn Leu
                1205                1210                1215
Ser Ser Glu Asp Glu Glu Leu Pro Cys Phe Gln His Leu Leu Phe Gly
            1220                1225                1230
Lys Val Asn Asn Ile Pro Ser Gln Ser Thr Arg His Ser Thr Val Ala
        1235                1240                1245
Thr Glu Cys Leu Ser Lys Asn Thr Glu Glu Asn Leu Leu Ser Leu Lys
    1250                1255                1260
Asn Ser Leu Asn Asp Cys Ser Asn Gln Val Ile Leu Ala Lys Ala Ser
1265                1270                1275                1280
Gln Glu His His Leu Ser Glu Glu Thr Lys Cys Ser Ala Ser Leu Phe
                1285                1290                1295
Ser Ser Gln Cys Ser Glu Leu Glu Asp Leu Thr Ala Asn Thr Asn Thr
            1300                1305                1310
Gln Asp Pro Phe Leu Ile Gly Ser Ser Lys Gln Met Arg His Gln Ser
        1315                1320                1325
Glu Ser Gln Gly Val Gly Leu Ser Asp Lys Glu Leu Val Ser Asp Asp
    1330                1335                1340
Glu Glu Arg Gly Thr Gly Leu Glu Glu Asn Asn Gln Glu Glu Gln Ser
1345                1350                1355                1360
Met Asp Ser Asn Leu Gly Glu Ala Ala Ser Gly Cys Glu Ser Glu Thr
                1365                1370                1375
Ser Val Ser Glu Asp Cys Ser Gly Leu Ser Ser Gln Ser Asp Ile Leu
            1380                1385                1390
Thr Thr Gln Gln Arg Asp Thr Met Gln His Asn Leu Ile Lys Leu Gln
        1395                1400                1405
Gln Glu Met Ala Glu Leu Glu Ala Val Leu Glu Gln His Gly Ser Gln
    1410                1415                1420
Pro Ser Asn Ser Tyr Pro Ser Ile Ile Ser Asp Ser Ser Ala Leu Glu
1425                1430                1435                1440
Asp Leu Arg Asn Pro Glu Gln Ser Thr Ser Glu Lys Ala Val Leu Thr
                1445                1450                1455
Ser Gln Lys Ser Ser Glu Tyr Pro Ile Ser Gln Asn Pro Glu Gly Leu
            1460                1465                1470
Ser Ala Asp Lys Phe Glu Val Ser Ala Asp Ser Ser Thr Ser Lys Asn
        1475                1480                1485
Lys Glu Pro Gly Val Glu Arg Ser Ser Pro Ser Lys Cys Pro Ser Leu
    1490                1495                1500
Asp Asp Arg Trp Tyr Met His Ser Cys Ser Gly Ser Leu Gln Asn Arg
1505                1510                1515                1520
Asn Tyr Pro Ser Gln Glu Glu Leu Ile Lys Val Val Asp Val Glu Glu
                1525                1530                1535
Gln Gln Leu Glu Glu Ser Gly Pro His Asp Leu Thr Glu Thr Ser Tyr
            1540                1545                1550
Leu Pro Arg Gln Asp Leu Glu Gly Thr Pro Tyr Leu Glu Ser Gly Ile
        1555                1560                1565
Ser Leu Phe Ser Asp Asp Pro Glu Ser Asp Pro Ser Glu Asp Arg Ala
    1570                1575                1580
Pro Glu Ser Ala Arg Val Gly Asn Ile Pro Ser Ser Thr Ser Ala Leu
```

```
                1585                1590                1595                1600
Lys Val Pro Gln Leu Lys Val Ala Glu Ser Ala Gln Ser Pro Ala Ala
                    1605                1610                1615

Ala His Thr Thr Asp Thr Ala Gly Tyr Asn Ala Met Glu Glu Ser Val
            1620                1625                1630

Ser Arg Glu Lys Pro Glu Leu Thr Ala Ser Thr Glu Arg Val Asn Lys
        1635                1640                1645

Arg Met Ser Met Val Val Ser Gly Leu Thr Pro Glu Glu Phe Met Leu
    1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
                1685                1690                1695

Cys Glu Arg Thr Leu Lys Tyr Phe Leu Gly Ile Ala Gly Gly Lys Trp
            1700                1705                1710

Val Val Ser Tyr Phe Trp Val Thr Gln Ser Ile Lys Glu Arg Lys Met
        1715                1720                1725

Leu Asn Glu His Asp Phe Glu Val Arg Gly Asp Val Val Asn Gly Arg
    1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
                1765                1770                1775

Thr Asp Gln Leu Glu Trp Met Val Gln Leu Cys Gly Ala Ser Val Val
            1780                1785                1790

Lys Glu Leu Ser Ser Phe Thr Leu Gly Thr Gly Val His Pro Ile Val
        1795                1800                1805

Val Val Gln Pro Asp Ala Trp Thr Glu Asp Asn Gly Phe His Ala Ile
    1810                1815                1820

Gly Gln Met Cys Glu Ala Pro Val Val Thr Arg Glu Trp Val Leu Asp
1825                1830                1835                1840

Ser Val Ala Leu Tyr Gln Cys Gln Glu Leu Asp Thr Tyr Leu Ile Pro
                1845                1850                1855

Gln Ile Pro His Ser His Tyr
            1860

(2) INFORMATION FOR SEQ ID NO: 5:

(i) SEQUENCE CHARACTERISTICS:
        (A) LENGTH: 5711 base pairs
        (B) TYPE: nucleic acid
        (C) STRANDEDNESS: Not Relevant
        (D) TOPOLOGY: linear (ii) MOLECULE TYPE: cDNA (vi) ORIGINAL SOURCE:
        (A) ORGANISM: Homo sapiens
        (B) STRAIN: BRCA1

(viii) POSITION IN GENOME:
        (A) CHROMOSOME/SEGMENT: 17
        (B) MAP POSITION: 17q21

(xi) SEQUENCE DESCRIPTION: SEQ ID NO: 5:

AGCTCGCTGA GACTTCCTGG ACCCCGCACC AGGCTGTGGG GTTTCTCAGA TAACTGGGCC      60

CCTGCGCTCA GGAGGCCTTC ACCCTCTGCT CTGGGTAAAG TTCATTGGAA CAGAAAGAAA     120

TGGATTTATC TGCTCTTCGC GTTGAAGAAG TACAAAATGT CATTAATGCT ATGCAGAAAA     180
```

```
TCTTAGAGTG TCCCATCTGT CTGGAGTTGA TCAAGGAACC TGTCTCCACA AAGTGTGACC    240

ACATATTTTG CAAATTTTGC ATGCTGAAAC TTCTCAACCA GAAGAAAGGG CCTTCACAGT    300

GTCCTTTATG TAAGAATGAT ATAACCAAAA GGAGCCTACA AGAAAGTACG AGATTTAGTC    360

AACTTGTTGA AGAGCTATTG AAAATCATTT GTGCTTTTCA GCTTGACACA GGTTTGGAGT    420

ATGCAAACAG CTATAATTTT GCAAAAAAGG AAAATAACTC TCCTGAACAT CTAAAAGATG    480

AAGTTTCTAT CATCCAAAGT ATGGGCTACA GAAACCGTGC CAAAAGACTT CTACAGAGTG    540

AACCCGAAAA TCCTTCCTTG CAGGAAACCA GTCTCAGTGT CCAACTCTCT AACCTTGGAA    600

CTGTGAGAAC TCTGAGGACA AGCAGCGGA TACAACCTCA AAAGACGTCT GTCTACATTG     660

AATTGGGATC TGATTCTTCT GAAGATACCG TTAATAAGGC AACTTATTGC AGTGTGGGAG    720

ATCAAGAATT GTTACAAATC ACCCCTCAAG GAACCAGGGA TGAAATCAGT TTGGATTCTG    780

CAAAAAAGGC TGCTTGTGAA TTTTCTGAGA CGGATGTAAC AAATACTGAA CATCATCAAC    840

CCAGTAATAA TGATTTGAAC ACCACTGAGA AGCGTGCAGC TGAGAGGCAT CCAGAAAAGT    900

ATCAGGGTAG TTCTGTTTCA AACTTGCATG TGGAGCCATG TGGCACAAAT ACTCATGCCA    960

GCTCATTACA GCATGAGAAC AGCAGTTTAT TACTCACTAA AGACAGAATG AATGTAGAAA   1020

AGGCTGAATT CTGTAATAAA AGCAAACAGC CTGGCTTAGC AAGGAGCCAA CATAACAGAT   1080

GGGCTGGAAG TAAGGAAACA TGTAATGATA GGCGGACTCC CAGCACAGAA AAAAAGGTAG   1140

ATCTGAATGC TGATCCCCTG TGTGAGAGAA AAGAATGGAA TAAGCAGAAA CTGCCATGCT   1200

CAGAGAATCC TAGAGATACT GAAGATGTTC CTTGGATAAC ACTAAATAGC AGCATTCAGA   1260

AAGTTAATGA GTGGTTTTCC AGAAGTGATG AACTGTTAGG TTCTGATGAC TCACATGATG   1320

GGGAGTCTGA ATCAAATGCC AAAGTAGCTG ATGTATTGGA CGTTCTAAAT GAGGTAGATG   1380

AATATTCTGG TTCTTCAGAG AAAATAGACT TACTGGCCAG TGATCCTCAT GAGGCTTTAA   1440

TATGTAAAAG TGAAAGAGTT CACTCCAAAT CAGTAGAGAG TAATATTGAA GACAAAATAT   1500

TTGGGAAAAC CTATCGGAAG AAGGCAAGCC TCCCCAACTT AAGCCATGTA ACTGAAAATC   1560

TAATTATAGG AGCATTTGTT ACTGAGCCAC AGATAATACA AGAGCGTCCC CTCACAAATA   1620

AATTAAAGCG TAAAAGGAGA CCTACATCAG GCCTTCATCC TGAGGATTTT ATCAAGAAAG   1680

CAGATTTGGC AGTTCAAAAG ACTCCTGAAA TGATAAATCA GGGAACTAAC CAAACGGAGC   1740

AGAATGGTCA AGTGATGAAT ATTACTAATA GTGGTCATGA GAATAAAACA AAAGGTGATT   1800

CTATTCAGAA TGAGAAAAAT CCTAACCCAA TAGAATCACT CGAAAAAGAA TCTGCTTTCA   1860

AAACGAAAGC TGAACCTATA AGCAGCAGTA TAAGCAATAT GGAACTCGAA TTAAATATCC   1920

ACAATTCAAA AGCACCTAAA AAGAATAGGC TGAGGAGGAA GTCTTCTACC AGGCATATTC   1980

ATGCGCTTGA ACTAGTAGTC AGTAGAAATC TAAGCCCACC TAATTGTACT GAATTGCAAA   2040

TTGATAGTTG TTCTAGCAGT GAAGAGATAA AGAAAAAAAA GTACAACCAA ATGCCAGTCA   2100

GGCACAGCAG AAACCTACAA CTCATGGAAG GTAAAGAACC TGCAACTGGA GCCAAGAAGA   2160

GTAACAAGCC AAATGAACAG ACAAGTAAAA GACATGACAG TGATACTTTC CCAGAGCTGA   2220

AGTTAACAAA TGCACCTGGT TCTTTTACTA AGTGTTCAAA TACCAGTGAA CTTAAAGAAT   2280

TTGTCAATCC TAGCCTTCCA AGAGAAGAAA AGAAGAGAA ACTAGAAACA GTTAAAGTGT     2340

CTAATAATGC TGAAGACCCC AAAGATCTCA TGTTAAGTGG AGAAAGGGTT TTGCAAACTG   2400

AAAGATCTGT AGAGAGTAGC AGTATTTCAC TGGTACCTGG TACTGATTAT GGCACTCAGG   2460

AAAGTATCTC GTTACTGGAA GTTAGCACTC TAGGGAAGGC AAAAACAGAA CCAAATAAAT   2520
```

```
GTGTGAGTCA GTGTGCAGCA TTTGAAAACC CCAAGGGACT AATTCATGGT TGTTCCAAAG    2580

ATAATAGAAA TGACACAGAA GGCTTTAAGT ATCCATTGGG ACATGAAGTT AACCACAGTC    2640

GGGAAACAAG CATAGAAATG GAAGAAAGTG AACTTGATGC TCAGTATTTG CAGAATACAT    2700

TCAAGGTTTC AAAGCGCCAG TCATTTGCTC TGTTTTCAAA TCCAGGAAAT GCAGAAGAGG    2760

AATGTGCAAC ATTCTCTGCC CACTCTGGGT CCTTAAAGAA ACAAAGTCCA AAAGTCACTT    2820

TTGAATGTGA ACAAAAGGAA GAAAATCAAG GAAAGAATGA GTCTAATATC AAGCCTGTAC    2880

AGACAGTTAA TATCACTGCA GGCTTTCCTG TGGTTGGTCA GAAAGATAAG CCAGTTGATA    2940

ATGCCAAATG TAGTATCAAA GGAGGCTCTA GGTTTTGTCT ATCATCTCAG TTCAGAGGCA    3000

ACGAAACTGG ACTCATTACT CCAAATAAAC ATGGACTTTT ACAAAACCCA TATCGTATAC    3060

CACCACTTTT TCCCATCAAG TCATTTGTTA AAACTAAATG TAAGAAAAAT CTGCTAGAGG    3120

AAAACTTTGA GGAACATTCA ATGTCACCTG AAAGAGAAAT GGGAAATGAG AACATTCCAA    3180

GTACAGTGAG CACAATTAGC CGTAATAACA TTAGAGAAAA TGTTTTTAAA GGAGCCAGCT    3240

CAAGCAATAT TAATGAAGTA GGTTCCAGTA CTAATGAAGT GGGCTCCAGT ATTAATGAAA    3300

TAGGTTCCAG TGATGAAAAC ATTCAAGCAG AACTAGGTAG AAACAGAGGG CCAAAATTGA    3360

ATGCTATGCT TAGATTAGGG GTTTTGCAAC CTGAGGTCTA TAAACAAAGT CTTCCTGGAA    3420

GTAATTGTAA GCATCCTGAA ATAAAAAAGC AAGAATATGA AGAAGTAGTT CAGACTGTTA    3480

ATACAGATTT CTCTCCATAT CTGATTTCAG ATAACTTAGA ACAGCCTATG GGAAGTAGTC    3540

ATGCATCTCA GGTTTGTTCT GAGACACCTG ATGACCTGTT AGATGATGGT GAAATAAAGG    3600

AAGATACTAG TTTTGCTGAA AATGACATTA AGGAAAGTTC TGCTGTTTTT AGCAAAAGCG    3660

TCCAGAGAGG AGAGCTTAGC AGGAGTCCTA GCCCTTTCAC CCATACACAT TTGGCTCAGG    3720

GTTACCGAAG AGGGGCCAAG AAATTAGAGT CCTCAGAAGA GAACTTATCT AGTGAGGATG    3780

AAGAGCTTCC CTGCTTCCAA CACTTGTTAT TTGGTAAAGT AAACAATATA CCTTCTCAGT    3840

CTACTAGGCA TAGCACCGTT GCTACCGAGT GTCTGTCTAA GAACACAGAG GAGAATTTAT    3900

TATCATTGAA GAATAGCTTA AATGACTGCA GTAACCAGGT AATATTGGCA AAGGCATCTC    3960

AGGAACATCA CCTTAGTGAG GAAACAAAAT GTTCTGCTAG CTTGTTTTCT TCACAGTGCA    4020

GTGAATTGGA AGACTTGACT GCAAATACAA ACACCCAGGA TCCTTTCTTG ATTGGTTCTT    4080

CCAAACAAAT GAGGCATCAG TCTGAAAGCC AGGGAGTTGG TCTGAGTGAC AAGGAATTGG    4140

TTTCAGATGA TGAAGAAAGA GGAACGGGCT TGGAAGAAAA TAATCAAGAA GAGCAAAGCA    4200

TGGATTCAAA CTTAGGTGAA GCAGCATCTG GGTGTGAGAG TGAAACAAGC GTCTCTGAAG    4260

ACTGCTCAGG GCTATCCTCT CAGAGTGACA TTTTAACCAC TCAGCAGAGG GATACCATGC    4320

AACATAACCT GATAAAGCTC CAGCAGGAAA TGGCTGAACT AGAAGCTGTG TTAGAACAGC    4380

ATGGGAGCCA GCCTTCTAAC AGCTACCCTT CCATCATAAG TGACTCTTCT GCCCTTGAGG    4440

ACCTGCGAAA TCCAGAACAA AGCACATCAG AAAAAGCAGT ATTAACTTCA CAGAAAAGTA    4500

GTGAATACCC TATAAGCCAG AATCCAGAAG GCCTTTCTGC TGACAAGTTT GAGGTGTCTG    4560

CAGATAGTTC TACCAGTAAA AATAAAGAAC CAGGAGTGGA AGGTCATCC CCTTCTAAAT    4620

GCCCATCATT AGATGATAGG TGGTACATGC ACAGTTGCTC TGGGAGTCTT CAGAATAGAA    4680

ACTACCCATC TCAAGAGGAG CTCATTAAGG TTGTTGATGT GGAGGAGCAA CAGCTGGAAG    4740

AGTCTGGGCC ACACGATTTG ACGGAAACAT CTTACTTGCC AAGGCAAGAT CTAGAGGGAA    4800

CCCCTTACCT GGAATCTGGA ATCAGCCTCT TCTCTGATGA CCCTGAATCT GATCCTTCTG    4860

AAGACAGAGC CCCAGAGTCA GCTCGTGTTG GCAACATACC ATCTTCAACC TCTGCATTGA    4920
```

-continued

```
AAGTTCCCCA ATTGAAAGTT GCAGAATCTG CCCAGGGTCC AGCTGCTGCT CATACTACTG      4980

ATACTGCTGG GTATAATGCA ATGGAAGAAA GTGTGAGCAG GGAGAAGCCA GAATTGACAG      5040

CTTCAACAGA AAGGGTCAAC AAAAGAATGT CCATGGTGGT GTCTGGCCTG ACCCCAGAAG      5100

AATTTATGCT CGTGTACAAG TTTGCCAGAA ACACCACAT CACTTTAACT AATCTAATTA       5160

CTGAAGAGAC TACTCATGTT GTTATGAAAA CAGATGCTGA GTTTGTGTGT GAACGGACAC      5220

TGAAATATTT TCTAGGAATT GCGGGAGGAA ATGGGTAGT TAGCTATTTC TGGGTGACCC       5280

AGTCTATTAA AGAAAGAAAA ATGCTGAATG AGCATGATTT TGAAGTCAGA GGAGATGTGG      5340

TCAATGGAAG AAACCACCAA GGTCCAAAGC GAGCAAGAGA ATCCCAGGAC AGAAAGATCT      5400

TCAGGGGGCT AGAAATCTGT TGCTATGGGC CCTTCACCAA CATGCCCACA GATCAACTGG      5460

AATGGATGGT ACAGCTGTGT GGTGCTTCTG TGGTGAAGGA GCTTTCATCA TTCACCCTTG      5520

GCACAGGTGT CCACCCAATT GTGGTTGTGC AGCCAGATGC CTGGACAGAG GACAATGGCT      5580

TCCATGCAAT TGGGCAGATG TGTGAGGCAC CTGTGGTGAC CCGAGAGTGG GTGTTGGACA      5640

GTGTAGCACT CTACCAGTGC CAGGAGCTGG ACACCTACCT GATACCCCAG ATCCCCCACA      5700

GCCACTACTG A                                                          5711
```

(2) INFORMATION FOR SEQ ID NO: 6:

(i) SEQUENCE CHARACTERISTICS:
        (A) LENGTH: 1863 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Homo sapiens
        (B) STRAIN: BRCA1

(viii) POSITION IN GENOME:
        (A) CHROMOSOME/SEGMENT: 17
        (B) MAP POSITION: 17q21

(xi) SEQUENCE DESCRIPTION: SEQ ID NO: 6:

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160
```

```
Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
                180                 185                 190

Lys Ala Thr Tyr Cys Ser Val Gly Asp Gln Glu Leu Leu Gln Ile Thr
                195                 200                 205

Pro Gln Gly Thr Arg Asp Glu Ile Ser Leu Asp Ser Ala Lys Lys Ala
            210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
                260                 265                 270

Pro Cys Gly Thr Asn Thr His Ala Ser Ser Leu Gln His Glu Asn Ser
            275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
                340                 345                 350

Trp Asn Lys Gln Lys Leu Pro Cys Ser Glu Asn Pro Arg Asp Thr Glu
            355                 360                 365

Asp Val Pro Trp Ile Thr Leu Asn Ser Ser Ile Gln Lys Val Asn Glu
            370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
                420                 425                 430

Ala Ser Asp Pro His Glu Ala Leu Ile Cys Lys Ser Glu Arg Val His
            435                 440                 445

Ser Lys Ser Val Glu Ser Asn Ile Glu Asp Lys Ile Phe Gly Lys Thr
    450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
            515                 520                 525

Pro Glu Met Ile Asn Gln Gly Thr Asn Gln Thr Glu Gln Asn Gly Gln
    530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575
```

```
Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
        610                 615                 620

Leu Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
        690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
850                 855                 860

Lys Arg Gln Ser Phe Ala Leu Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
        930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
```

-continued

```
              995                1000               1005
Ser Pro Glu Arg Glu Met Gly Asn Glu Asn Ile Pro Ser Thr Val Ser
    1010               1015               1020

Thr Ile Ser Arg Asn Asn Ile Arg Glu Asn Val Phe Lys Gly Ala Ser
1025               1030               1035               1040

Ser Ser Asn Ile Asn Glu Val Gly Ser Ser Thr Asn Glu Val Gly Ser
                1045               1050               1055

Ser Ile Asn Glu Ile Gly Ser Ser Asp Glu Asn Ile Gln Ala Glu Leu
        1060               1065               1070

Gly Arg Asn Arg Gly Pro Lys Leu Asn Ala Met Leu Arg Leu Gly Val
            1075               1080               1085

Leu Gln Pro Glu Val Tyr Lys Gln Ser Leu Pro Gly Ser Asn Cys Lys
    1090               1095               1100

His Pro Glu Ile Lys Lys Gln Glu Tyr Glu Glu Val Val Gln Thr Val
1105               1110               1115               1120

Asn Thr Asp Phe Ser Pro Tyr Leu Ile Ser Asp Asn Leu Glu Gln Pro
                1125               1130               1135

Met Gly Ser Ser His Ala Ser Gln Val Cys Ser Glu Thr Pro Asp Asp
            1140               1145               1150

Leu Leu Asp Asp Gly Glu Ile Lys Glu Asp Thr Ser Phe Ala Glu Asn
        1155               1160               1165

Asp Ile Lys Glu Ser Ser Ala Val Phe Ser Lys Ser Val Gln Arg Gly
    1170               1175               1180

Glu Leu Ser Arg Ser Pro Ser Pro Phe Thr His Thr His Leu Ala Gln
1185               1190               1195               1200

Gly Tyr Arg Arg Gly Ala Lys Lys Leu Glu Ser Ser Glu Glu Asn Leu
                1205               1210               1215

Ser Ser Glu Asp Glu Glu Leu Pro Cys Phe Gln His Leu Leu Phe Gly
            1220               1225               1230

Lys Val Asn Asn Ile Pro Ser Gln Ser Thr Arg His Ser Thr Val Ala
        1235               1240               1245

Thr Glu Cys Leu Ser Lys Asn Thr Glu Glu Asn Leu Leu Ser Leu Lys
    1250               1255               1260

Asn Ser Leu Asn Asp Cys Ser Asn Gln Val Ile Leu Ala Lys Ala Ser
1265               1270               1275               1280

Gln Glu His His Leu Ser Glu Thr Lys Cys Ser Ala Ser Leu Phe
                1285               1290               1295

Ser Ser Gln Cys Ser Glu Leu Glu Asp Leu Thr Ala Asn Thr Asn Thr
            1300               1305               1310

Gln Asp Pro Phe Leu Ile Gly Ser Ser Lys Gln Met Arg His Gln Ser
        1315               1320               1325

Glu Ser Gln Gly Val Gly Leu Ser Asp Lys Glu Leu Val Ser Asp Asp
    1330               1335               1340

Glu Glu Arg Gly Thr Gly Leu Glu Glu Asn Asn Gln Glu Glu Gln Ser
1345               1350               1355               1360

Met Asp Ser Asn Leu Gly Glu Ala Ala Ser Gly Cys Glu Ser Glu Thr
                1365               1370               1375

Ser Val Ser Glu Asp Cys Ser Gly Leu Ser Ser Gln Ser Asp Ile Leu
            1380               1385               1390

Thr Thr Gln Gln Arg Asp Thr Met Gln His Asn Leu Ile Lys Leu Gln
        1395               1400               1405

Gln Glu Met Ala Glu Leu Glu Ala Val Leu Glu Gln His Gly Ser Gln
    1410               1415               1420
```

-continued

```
Pro Ser Asn Ser Tyr Pro Ser Ile Ile Ser Asp Ser Ser Ala Leu Glu
1425                1430                1435                1440

Asp Leu Arg Asn Pro Glu Gln Ser Thr Ser Glu Lys Ala Val Leu Thr
            1445                1450                1455

Ser Gln Lys Ser Ser Glu Tyr Pro Ile Ser Gln Asn Pro Glu Gly Leu
        1460                1465                1470

Ser Ala Asp Lys Phe Glu Val Ser Ala Asp Ser Ser Thr Ser Lys Asn
    1475                1480                1485

Lys Glu Pro Gly Val Glu Arg Ser Ser Pro Ser Lys Cys Pro Ser Leu
1490                1495                1500

Asp Asp Arg Trp Tyr Met His Ser Cys Ser Gly Ser Leu Gln Asn Arg
1505                1510                1515                1520

Asn Tyr Pro Ser Gln Glu Glu Leu Ile Lys Val Val Asp Val Glu Glu
                1525                1530                1535

Gln Gln Leu Glu Glu Ser Gly Pro His Asp Leu Thr Glu Thr Ser Tyr
            1540                1545                1550

Leu Pro Arg Gln Asp Leu Glu Gly Thr Pro Tyr Leu Glu Ser Gly Ile
        1555                1560                1565

Ser Leu Phe Ser Asp Asp Pro Glu Ser Asp Pro Ser Glu Asp Arg Ala
    1570                1575                1580

Pro Glu Ser Ala Arg Val Gly Asn Ile Pro Ser Ser Thr Ser Ala Leu
1585                1590                1595                1600

Lys Val Pro Gln Leu Lys Val Ala Glu Ser Ala Gln Gly Pro Ala Ala
                1605                1610                1615

Ala His Thr Thr Asp Thr Ala Gly Tyr Asn Ala Met Glu Glu Ser Val
            1620                1625                1630

Ser Arg Glu Lys Pro Glu Leu Thr Ala Ser Thr Glu Arg Val Asn Lys
        1635                1640                1645

Arg Met Ser Met Val Val Ser Gly Leu Thr Pro Glu Glu Phe Met Leu
    1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
                1685                1690                1695

Cys Glu Arg Thr Leu Lys Tyr Phe Leu Gly Ile Ala Gly Gly Lys Trp
            1700                1705                1710

Val Val Ser Tyr Phe Trp Val Thr Gln Ser Ile Lys Glu Arg Lys Met
        1715                1720                1725

Leu Asn Glu His Asp Phe Glu Val Arg Gly Asp Val Val Asn Gly Arg
    1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
                1765                1770                1775

Thr Asp Gln Leu Glu Trp Met Val Gln Leu Cys Gly Ala Ser Val Val
            1780                1785                1790

Lys Glu Leu Ser Ser Phe Thr Leu Gly Thr Gly Val His Pro Ile Val
        1795                1800                1805

Val Val Gln Pro Asp Ala Trp Thr Glu Asp Asn Gly Phe His Ala Ile
    1810                1815                1820

Gly Gln Met Cys Glu Ala Pro Val Val Thr Arg Glu Trp Val Leu Asp
1825                1830                1835                1840
```

```
Ser Val Ala Leu Tyr Gln Cys Gln Glu Leu Asp Thr Tyr Leu Ile Pro
            1845                1850                1855

Gln Ile Pro His Ser His Tyr
        1860
```

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 2F primer (xi) SEQUENCE DESCRIPTION: SEQ ID NO: 7:

GAAGTTGTCA TTTTATAAAC CTTT                      24

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 2R primer (xi) SEQUENCE DESCRIPTION: SEQ ID NO: 8:

TGTCTTTTCT TCCCTAGTAT GT                        22

(2) INFORMATION FOR SEQ ID NO: 9:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 3F primer (xi) SEQUENCE DESCRIPTION: SEQ ID NO: 9:

TCCTGACACA GCAGACATTT A                         21

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 3R primer (xi) SEQUENCE DESCRIPTION: SEQ ID NO: 10:

TTGGATTTTC GTTCTCACTT A                         21

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 5F primer (xi) SEQUENCE DESCRIPTION: SEQ ID NO: 11:

CTCTTAAGGG CAGTTGTGAG                                           20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 5R-M13* primer (xi) SEQUENCE DESCRIPTION: SEQ ID NO: 12:

TTCCTACTGT GGTTGCTTCC                                           20

(2) INFORMATION FOR SEQ ID NO: 13:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 6/7F primer (xi) SEQUENCE DESCRIPTION: SEQ ID NO: 13:

CTTATTTTAG TGTCCTTAAA AGG                                       23

(2) INFORMATION FOR SEQ ID NO: 14:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 6R (xi) SEQUENCE DESCRIPTION: SEQ ID NO: 14:

TTTCATGGAC AGCACTTGAG TG                                        22

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: linear

```
        (ii) MOLECULE TYPE: DNA (genomic)

(vi) ORIGINAL SOURCE:
             (B) STRAIN: 7F primer (xi) SEQUENCE DESCRIPTION: SEQ ID NO: 15:

CACAACAAAG AGCATACATA GGG                                              23

(2) INFORMATION FOR SEQ ID NO: 16:

(i) SEQUENCE CHARACTERISTICS:
            (A) LENGTH: 20 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
             (B) STRAIN: 6/7R primer (xi) SEQUENCE DESCRIPTION: SEQ ID NO: 16:

TCGGGTTCAC TCTGTAGAAG                                                  20

(2) INFORMATION FOR SEQ ID NO: 17:

(i) SEQUENCE CHARACTERISTICS:
            (A) LENGTH: 21 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
             (B) STRAIN: 8F1 primer (xi) SEQUENCE DESCRIPTION: SEQ ID NO: 17:

TTCTCTTCAG GAGGAAAAGC A                                                21

(2) INFORMATION FOR SEQ ID NO: 18:

(i) SEQUENCE CHARACTERISTICS:
            (A) LENGTH: 21 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
             (B) STRAIN: 8R1 primer (xi) SEQUENCE DESCRIPTION: SEQ ID NO: 18:

GCTGCCTACC ACAAATACAA A                                                21

(2) INFORMATION FOR SEQ ID NO: 19:

(i) SEQUENCE CHARACTERISTICS:
            (A) LENGTH: 23 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
             (B) STRAIN: 9F primer (xi) SEQUENCE DESCRIPTION: SEQ ID NO: 19:
```

```
CCACAGTAGA TGCTCAGTAA ATA                                              23

(2) INFORMATION FOR SEQ ID NO: 20:

(i) SEQUENCE CHARACTERISTICS:
          (A) LENGTH: 23 base pairs
          (B) TYPE: nucleic acid
          (C) STRANDEDNESS: Not Relevant
          (D) TOPOLOGY: linear (ii) MOLECULE TYPE: DNA (genomic)

(vi) ORIGINAL SOURCE:
          (B) STRAIN: 9R primer (xi) SEQUENCE DESCRIPTION: SEQ ID NO: 20:

TAGGAAAATA CCAGCTTCAT AGA                                              23

(2) INFORMATION FOR SEQ ID NO: 21:

(i) SEQUENCE CHARACTERISTICS:
          (A) LENGTH: 20 base pairs
          (B) TYPE: nucleic acid
          (C) STRANDEDNESS: Not Relevant
          (D) TOPOLOGY: linear (ii) MOLECULE TYPE: DNA (genomic)

(vi) ORIGINAL SOURCE:
          (B) STRAIN: 10F primer (xi) SEQUENCE DESCRIPTION: SEQ ID NO: 21:

TGGTCAGCTT TCTGTAATCG                                                  20

(2) INFORMATION FOR SEQ ID NO: 22:

(i) SEQUENCE CHARACTERISTICS:
          (A) LENGTH: 24 base pairs
          (B) TYPE: nucleic acid
          (C) STRANDEDNESS: Not Relevant
          (D) TOPOLOGY: linear (ii) MOLECULE TYPE: DNA (genomic)

(vi) ORIGINAL SOURCE:
          (B) STRAIN: 10R primer (xi) SEQUENCE DESCRIPTION: SEQ ID NO: 22:

GTATCTACCC ACTCTCTTCT TCAG                                             24

(2) INFORMATION FOR SEQ ID NO: 23:

(i) SEQUENCE CHARACTERISTICS:
          (A) LENGTH: 19 base pairs
          (B) TYPE: nucleic acid
          (C) STRANDEDNESS: Not Relevant
          (D) TOPOLOGY: linear (ii) MOLECULE TYPE: DNA (genomic)

(vi) ORIGINAL SOURCE:
          (B) STRAIN: 11AF primer (xi) SEQUENCE DESCRIPTION: SEQ ID NO: 23:

CCACCTCCAA GGTGTATCA                                                   19

(2) INFORMATION FOR SEQ ID NO: 24:

(i) SEQUENCE CHARACTERISTICS:
```

```
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11AR primer (xi) SEQUENCE DESCRIPTION: SEQ ID NO: 24:

TGTTATGTTG GCTCCTTGCT                                             20

(2) INFORMATION FOR SEQ ID NO: 25:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11BF1 primer (xi) SEQUENCE DESCRIPTION: SEQ ID NO: 25:

CACTAAAGAC AGAATGAATC TA                                          22

(2) INFORMATION FOR SEQ ID NO: 26:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11BR1 primer (xi) SEQUENCE DESCRIPTION: SEQ ID NO: 26:

GAAGAACCAG AATATTCATC TA                                          22

(2) INFORMATION FOR SEQ ID NO: 27:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11CF1 primer (xi) SEQUENCE DESCRIPTION: SEQ ID NO: 27:

TGATGGGGAG TCTGAATCAA                                             20

(2) INFORMATION FOR SEQ ID NO: 28:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)
```

(vi) ORIGINAL SOURCE:
            (B) STRAIN: 11CR1 primer (xi) SEQUENCE DESCRIPTION: SEQ ID NO: 28:

TCTGCTTTCT TGATAAAATC CT                                                  22

(2) INFORMATION FOR SEQ ID NO: 29:

(i) SEQUENCE CHARACTERISTICS:
            (A) LENGTH: 20 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
            (B) STRAIN: 11DF1 primer (xi) SEQUENCE DESCRIPTION: SEQ ID NO: 29:

AGCGTCCCCT CACAAATAAA                                                     20

(2) INFORMATION FOR SEQ ID NO: 30:

(i) SEQUENCE CHARACTERISTICS:
            (A) LENGTH: 20 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
            (B) STRAIN: 11DR1 primer (xi) SEQUENCE DESCRIPTION: SEQ ID NO: 30:

TCAAGCGCAT GAATATGCCT                                                     20

(2) INFORMATION FOR SEQ ID NO: 31:

(i) SEQUENCE CHARACTERISTICS:
            (A) LENGTH: 22 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
            (B) STRAIN: 11EF primer (xi) SEQUENCE DESCRIPTION: SEQ ID NO: 31:

GTATAAGCAA TATGGAACTC GA                                                  22

(2) INFORMATION FOR SEQ ID NO: 32:

(i) SEQUENCE CHARACTERISTICS:
            (A) LENGTH: 23 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
            (B) STRAIN: 11ER primer (xi) SEQUENCE DESCRIPTION: SEQ ID NO: 32:

TTAAGTTCACT GGTATTTGAA CA                                                 23

(2) INFORMATION FOR SEQ ID NO: 33:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11FF primer (xi) SEQUENCE DESCRIPTION: SEQ ID NO: 33:

GACAGCGATA CTTTCCCAGA                                       20

(2) INFORMATION FOR SEQ ID NO: 34:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11FR primer (xi) SEQUENCE DESCRIPTION: SEQ ID NO: 34:

TGGAACAACC ATGAATTAGT C                                      21

(2) INFORMATION FOR SEQ ID NO: 35:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11GF primer (xi) SEQUENCE DESCRIPTION: SEQ ID NO: 35:

GGAAGTTAGC ACTCTAGGGA                                       20

(2) INFORMATION FOR SEQ ID NO: 36:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11GR primer (xi) SEQUENCE DESCRIPTION: SEQ ID NO: 36:

GCAGTGATAT TAACTGTCTG TA                                     22

(2) INFORMATION FOR SEQ ID NO: 37:

(i) SEQUENCE CHARACTERISTICS:
        (A) LENGTH: 22 base pairs
        (B) TYPE: nucleic acid
        (C) STRANDEDNESS: Not Relevant (D) TOPOLOGY: linear (ii) MOLECULE TYPE: DNA (genomic)

(vi) ORIGINAL SOURCE:
            (B) STRAIN: 11HF primer (xi) SEQUENCE DESCRIPTION: SEQ ID NO: 37:

TGGGTCCTTA AGAAACAAA GT                                          22

(2) INFORMATION FOR SEQ ID NO: 38:

(i) SEQUENCE CHARACTERISTICS:
            (A) LENGTH: 21 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
            (B) STRAIN: 11HR primer (xi) SEQUENCE DESCRIPTION: SEQ ID NO: 38:

TCAGGTGACA TTGAATCTTC C                                          21

(2) INFORMATION FOR SEQ ID NO: 39:

(i) SEQUENCE CHARACTERISTICS:
            (A) LENGTH: 21 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
            (B) STRAIN: 11IF primer (xi) SEQUENCE DESCRIPTION: SEQ ID NO: 39:

CCACTTTTTC CCATCAAGTC A                                          21

(2) INFORMATION FOR SEQ ID NO: 40:

(i) SEQUENCE CHARACTERISTICS:
            (A) LENGTH: 22 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
            (B) STRAIN: 11IR primer (xi) SEQUENCE DESCRIPTION: SEQ ID NO: 40:

TCAGGATGCT TACAATTACT TC                                         22

(2) INFORMATION FOR SEQ ID NO: 41:

(i) SEQUENCE CHARACTERISTICS:
            (A) LENGTH: 23 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
            (B) STRAIN: 11JF primer

```
    (xi) SEQUENCE DESCRIPTION: SEQ ID NO: 41:

CAAAATTGAA TGCTATGCTT AGA                                           23

(2) INFORMATION FOR SEQ ID NO: 42:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11JR primer (xi) SEQUENCE DESCRIPTION: SEQ ID NO: 42:

TCGGTAACCC TGAGCCAAAT                                               20

(2) INFORMATION FOR SEQ ID NO: 43:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11KF primer (xi) SEQUENCE DESCRIPTION: SEQ ID NO: 43:

GCAAAAGCGT CCAGAAAGGA                                               20

(2) INFORMATION FOR SEQ ID NO: 44:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11KR-1 primer (xi) SEQUENCE DESCRIPTION: SEQ ID NO: 44:

TATTTGCAGT CAAGTCTTCC AA                                            22

(2) INFORMATION FOR SEQ ID NO: 45:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11LF-1 primer (xi) SEQUENCE DESCRIPTION: SEQ ID NO: 45:

GTAATATTGG CAAAGGCATC T                                             21

(2) INFORMATION FOR SEQ ID NO: 46:
```

(i) SEQUENCE CHARACTERISTICS:
    (A) LENGTH: 22 base pairs
    (B) TYPE: nucleic acid
    (C) STRANDEDNESS: Not Relevant
    (D) TOPOLOGY: linear (ii) MOLECULE TYPE: DNA (genomic)

(vi) ORIGINAL SOURCE:
    (B) STRAIN: 11LR primer (xi) SEQUENCE DESCRIPTION: SEQ ID NO: 46:

TAAAATGTGC TCCCCAAAAG CA                    22

(2) INFORMATION FOR SEQ ID NO: 47:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 12F primer (xi) SEQUENCE DESCRIPTION: SEQ ID NO: 47:

GTCCTGCCAA TGAGAAGAAA                       20

(2) INFORMATION FOR SEQ ID NO: 48:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 12R primer (xi) SEQUENCE DESCRIPTION: SEQ ID NO: 48:

TGTCAGCAAA CCTAAGAATG T                     21

(2) INFORMATION FOR SEQ ID NO: 49:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 13F primer (xi) SEQUENCE DESCRIPTION: SEQ ID NO: 49:

AATGGAAAGC TTCTCAAAGT A                     21

(2) INFORMATION FOR SEQ ID NO: 50:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
            (B) STRAIN: 13R primer (xi) SEQUENCE DESCRIPTION: SEQ ID NO: 50:

ATGTTGGAGC TAGGTCCTTA C                                              21

(2) INFORMATION FOR SEQ ID NO: 51:

(i) SEQUENCE CHARACTERISTICS:
            (A) LENGTH: 22 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
            (B) STRAIN: 14F primer (xi) SEQUENCE DESCRIPTION: SEQ ID NO: 51:

CTAACCTGAA TTATCACTAT CA                                             22

(2) INFORMATION FOR SEQ ID NO: 52:

(i) SEQUENCE CHARACTERISTICS:
            (A) LENGTH: 21 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
            (B) STRAIN: 14R primer (xi) SEQUENCE DESCRIPTION: SEQ ID NO: 52:

GTGTATAAAT GCCTGTATGC A                                              21

(2) INFORMATION FOR SEQ ID NO: 53:

(i) SEQUENCE CHARACTERISTICS:
            (A) LENGTH: 19 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
            (B) STRAIN: 15F primer (xi) SEQUENCE DESCRIPTION: SEQ ID NO: 53:

TGGCTGCCCA GGAAGTATG                                                 19

(2) INFORMATION FOR SEQ ID NO: 54:

(i) SEQUENCE CHARACTERISTICS:
            (A) LENGTH: 23 base pairs
            (B) TYPE: nucleic acid
            (C) STRANDEDNESS: Not Relevant
            (D) TOPOLOGY: linear (ii) MOLECULE TYPE: DNA (genomic)

(vi) ORIGINAL SOURCE:
            (B) STRAIN: 15R primer (xi) SEQUENCE DESCRIPTION: SEQ ID NO: 54:

AACCAGAATA TCTTTATGTA GGA                                            23

-continued (2) INFORMATION FOR SEQ ID NO: 55:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 16F primer (xi) SEQUENCE DESCRIPTION: SEQ ID NO: 55:

AATTCTTAAC AGAGACCAGA AC                                    22

(2) INFORMATION FOR SEQ ID NO: 56:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 16R primer (xi) SEQUENCE DESCRIPTION: SEQ ID NO: 56:

AAAACTCTTT CCAGAATGTT GT                                    22

(2) INFORMATION FOR SEQ ID NO: 57:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 17F primer (xi) SEQUENCE DESCRIPTION: SEQ ID NO: 57:

GTGTAGAACG TGCAGGATTG                                        20

(2) INFORMATION FOR SEQ ID NO: 58:

(i) SEQUENCE CHARACTERISTICS:
        (A) LENGTH: 18 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 17R primer (xi) SEQUENCE DESCRIPTION: SEQ ID NO: 58:

TCGCCTCATG TGGTTTTA                                            18

(2) INFORMATION FOR SEQ ID NO: 59:

(i) SEQUENCE CHARACTERISTICS:
        (A) LENGTH: 21 base pairs
        (B) TYPE: nucleic acid

```
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 18F primer (xi) SEQUENCE DESCRIPTION: SEQ ID NO: 59:

GGCTCTTTAG CTTCTTAGGA C                                         21

(2) INFORMATION FOR SEQ ID NO: 60:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 18R primer (xi) SEQUENCE DESCRIPTION: SEQ ID NO: 60:

GAGACCATTT TCCCAGCATC                                           20

(2) INFORMATION FOR SEQ ID NO: 61:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 19F primer (xi) SEQUENCE DESCRIPTION: SEQ ID NO: 61:

CTGTCATTCT TCCTGTGCTC                                           20

(2) INFORMATION FOR SEQ ID NO: 62:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 19R primer (xi) SEQUENCE DESCRIPTION: SEQ ID NO: 62:

CATTGTTAAG GAAAGTGGTG C                                         21

(2) INFORMATION FOR SEQ ID NO: 63:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 20F primer
```

-continued (xi) SEQUENCE DESCRIPTION: SEQ ID NO: 63:

ATATGACGTG TCTGCTCCAC                                                20

(2) INFORMATION FOR SEQ ID NO: 64:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 20R primer (xi) SEQUENCE DESCRIPTION: SEQ ID NO: 64:

GGGAATCCAA ATTACACAGC                                                20

(2) INFORMATION FOR SEQ ID NO: 65:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 21F primer (xi) SEQUENCE DESCRIPTION: SEQ ID NO: 65:

AAGCTCTTCC TTTTTGAAAG TC                                             22

(2) INFORMATION FOR SEQ ID NO: 66:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 21R primer (xi) SEQUENCE DESCRIPTION: SEQ ID NO: 66:

GTAGAGAAAT AGAATAGCCT CT                                             22

(2) INFORMATION FOR SEQ ID NO: 67:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 22F primer (xi) SEQUENCE DESCRIPTION: SEQ ID NO: 67:

TCCCATTGAG AGGTCTTGCT                                                20

(2) INFORMATION FOR SEQ ID NO: 68:

```
    (i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 22R primer (xi) SEQUENCE DESCRIPTION: SEQ ID NO: 68:

GAGAAGACTT CTGAGGCTAC                                              20

(2) INFORMATION FOR SEQ ID NO: 69:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 23F-1 primer (xi) SEQUENCE DESCRIPTION: SEQ ID NO: 69:

TGAAGTGACA GTTCCAGTAG T                                            21

(2) INFORMATION FOR SEQ ID NO: 70:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 23R-1 primer (xi) SEQUENCE DESCRIPTION: SEQ ID NO: 70:

CATTTTAGCC ATTCATTCAA CAA                                          23

(2) INFORMATION FOR SEQ ID NO: 71:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 24F primer (xi) SEQUENCE DESCRIPTION: SEQ ID NO: 71:

ATGAATTGAC ACTAATCTCT GC                                           22

(2) INFORMATION FOR SEQ ID NO: 72:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear
```

-continued

```
(ii) MOLECULE TYPE: DNA (genomic)

(vi) ORIGINAL SOURCE:
     (B) STRAIN: 24R primer (xi) SEQUENCE DESCRIPTION: SEQ ID NO: 72:

GTAGCCAGGA CAGTAGAAGG A                                               21
```